United States Patent
Antel et al.

(10) Patent No.: US 7,547,708 B2
(45) Date of Patent: Jun. 16, 2009

(54) N-SULFAMOYL-N'-BENZOPYRANPIPERIDINE COMPOUNDS AND USES THEREOF

(75) Inventors: Jochen Antel, Bad Muender (DE); Harald Waldeck, Isernhagen HB (DE); Uwe Schoen, Burgdorf (DE); Peter-Colin Gregory, Hannover (DE); Michael Wurl, Garbsen (DE); Michael Firnges, Barsinghausen (DE); Dania Reiche, Adelheidsdorf (DE); Uwe Reinecker, Ronnenberg (DE); Holger Sann, Hannover (DE)

(73) Assignee: Solvay Pharmaceuticals, Inc., Hannover (DE)

( * ) Notice: Subject to any disclaimer, the term of this patent is extended or adjusted under 35 U.S.C. 154(b) by 11 days.

(21) Appl. No.: 11/598,684

(22) Filed: Nov. 14, 2006

(65) Prior Publication Data

US 2007/0117823 A1    May 24, 2007

Related U.S. Application Data

(60) Provisional application No. 60/736,634, filed on Nov. 14, 2005.

(51) Int. Cl.
*A61K 31/438* (2006.01)
*C07D 491/10* (2006.01)

(52) U.S. Cl. .......... 514/278; 546/17; 544/124; 544/360; 514/232.8; 514/253

(58) Field of Classification Search ............... 514/278, 514/253, 232.8; 546/17; 544/124, 360
See application file for complete search history.

(56) References Cited

U.S. PATENT DOCUMENTS 5,206,240 A    4/1993    Baldwin et al.

6,946,243 B2    9/2005    Hebebrand et al.
2007/0027118 A1*    2/2007    Cheng et al. .......... 514/151

FOREIGN PATENT DOCUMENTS

| EP | 0 431 943 A2 | 5/1991 |
|----|---|---|
| JP | 2005-119987 A | 5/2005 |
| WO | WO 95/30642 A1 | 11/1995 |
| WO | WO 02/07821 A1 | 1/2002 |
| WO | WO 2004/092179 A1 | 10/2004 |

OTHER PUBLICATIONS

Camille G. Wermuth, "Molecular Variations Based on Isosteric Replacements", The Practive of Medicinal Chemistry, Academic Press Limited, 1996, pp. 203-237.

* cited by examiner

*Primary Examiner*—Charanjit S Aulakh
(74) *Attorney, Agent, or Firm*—Crowell & Morning LLP

(57) ABSTRACT

N-sulfamoyl-N'-benzopyranpiperidine compounds of formula I and their physiologically acceptable acid addition salts, pharmaceutical compositions comprising them, processes for their preparation, and their use for the treatment and/or inhibition of glaucoma, epilepsy, bipolar disorders, migraine, neuropathic pain, obesity, type II diabetes, metabolic syndrome, alcohol dependence, and/or cancer, and related concomitant and/or secondary diseases or conditions

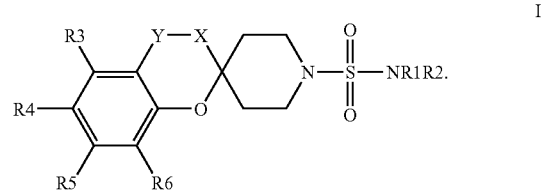

20 Claims, No Drawings

N-SULFAMOYL-N'-BENZOPYRANPIPERIDINE COMPOUNDS AND USES THEREOF

BACKGROUND OF THE INVENTION

The present invention relates to novel N-sulfamoyl-N'-benzopyranpiperidines and their physiologically acceptable acid addition salts, to pharmaceutical compositions comprising them, processes for their preparation, and their use for the treatment and/or inhibition of glaucoma, epilepsy, bipolar disorders, migraine, neuropathic pain, obesity, type II diabetes, metabolic syndrome, alcohol dependence, and/or cancer, and its concomitant and/or secondary diseases or conditions.

Some 4-oxospiro[benzopyran-2,4'-piperdines] and their uses as Class III antiarrhythmic agents are described by Elliott et al. (J. Med. Chem. 1992, 35, 3973 to 3976). Similar compounds and their uses as selective alpha1a-adrenergic receptor antagonists are also described by Nerenberg et al. (Bioorganic & Medical Chemistry Letters 1999, 9, 291 to 294).

Yamato et. al. (J. Med. Chem. 1981, 24, 194 to 198) disclose synthesis and structure-activity relationship of spiro [isochromanpiperidine] analogues for inhibition of histamine release.

Fletcher et al. (J. Med. Chem. 2002, 45, 492 to 503) report on 4-(phenylsulfonyl)piperdines, their synthesis and use as bioavailable 5-HT2A receptor antagonists.

U.S. Pat. No. 5,206,240 (=EP 431,943) teaches substituted spirocycles and their use as Class III antiarrhythmic agents, and positive inotropic or cardiotonic agents. U.S. Pat. No. 5,206,240 is also concerned with pharmaceutical formulations comprising one or more of the novel compounds as active ingredient, either alone or in combination with one or more of a Class I, Class II or Class IV antiarrhythmic agent.

A method of discovering compounds suitable for the treatment and/or prophylaxis of obesity by inhibiting lipogenesis via the inhibition of carbonic anhydrases in mammals and humans is known from U.S. Pat. No. 6,946,243 (=WO 02/07821).

SUMMARY OF THE INVENTION

It was an object of the present invention to provide new pharmaceutically active compounds which inhibit carbonic anydrase.

Another object of the invention was to provide compounds and compositions useful for treatment and/or inhibition of conditions such as glaucoma, epilepsy, bipolar disorders, migraine, neuropathic pain, obesity, type II diabetes, metabolic syndrome, alcohol dependence, and/or cancer, and its concomitant and/or secondary diseases or conditions.

A further object of the invention was to provide a method of treating or inhibiting a condition or disease state selected from the group consisting of glaucoma, epilepsy, bipolar disorders, migraine, neuropathic pain, obesity, type II diabetes, metabolic syndrome, alcohol dependence, and/or cancer, and concomitant and/or secondary diseases or conditions.

It was also an object of the invention to provide an effective method of producing such compounds.

It has now surprisingly been found that certain novel N-sulfamoyl-N'-benzopyranpiperidines and their physiologically acceptable acid addition salts are suitable for the treatment and/or inhibition of glaucoma, epilepsy, bipolar disorders, migraine, neuropathic pain, obesity, type II diabetes, metabolic syndrome, alcohol dependence, and/or cancer, and its concomitant and/or secondary diseases or conditions.

According to the invention, a compound of general Formula I,

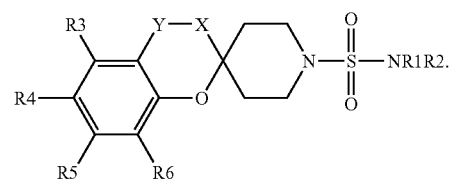

In which R1 and R2 are independently selected from the group consisting of hydrogen, $C_1$ to $C_4$ alkyl, $C_4$ to $C_7$ cycloalkyl, or wherein R1 and R2 together form a 5 or 6-membered ring which optionally may contain from 1 to 2 heteroatoms independently selected from the group consisting of nitrogen and/or oxygen atoms and which may also be substituted by optionally substituted aryl, optionally substituted heteroaryl or arylenehalogenalkyl;

wherein R3 to R6 are independently selected from the group consisting of: hydrogen; halogen; $C_1$ to $C_4$ alkyl; $C_2$ to $C_4$ alkenyl, optionally substituted with aryl; $C_1$ to $C_4$ alkoxy; $C_1$ to $C_4$ alkoxy substituted with halogen provided that the alpha-carbon atom is substituted by no other halogen than fluorine if any; $C_2$ to $C_4$ alkinyl; $C_1$ to $C_4$ $NSO_2$alkyl; $NH_2$; $NO_2$; $C_1$ to $C_4$ aminoalkyl; $C_2$ to $C_8$ aminodialkyl; cyano; oxyaryl; oxyalkylenearyl; oxyarylenealkyl; oxyalkylene-arylenealkoxy; $C_2$ to $C_8$ ester (e.g., oxycarbonyl $C_1$ to $C_7$ alkyl); $C_1$ to $C_8$ amido; $C_2$ to $C_8$ oxyalkylenecarbonylalkyl; $C_2$ to $C_8$ oxyalkyleneoxyalkyl; $C_1$ to $C_4$ amidooxyalkyl; aryl, optionally substituted; heteroaryl, optionally substituted; condensed aryl, optionally substituted; condensed heteroaryl, optionally substituted; and or;

wherein R3 and R6 have the same meaning as above and wherein R4 and R5 together form a 5 or 6-membered ring which may optionally contain from 1 to 3 heteroatoms independently selected from the group consisting of: nitrogen, oxygen and sulfur and which may optionally bear 1 or 2 double bonds, which may also contain a carbonyl group and which may also be substituted by $C_1$ to $C_4$ alkyl, $C_1$ to $C_4$ halogenalkyl, optionally substituted aryl, and/or optionally substituted heteroaryl;

or; wherein R5 and R6 have the same meaning as above and wherein R3 and R4 together form a 5 or 6-membered ring which may optionally contain from 1 to 3 heteroatoms independently selected from the group consisting of: nitrogen, oxygen and sulfur and which may optionally bear 1 or 2 double bonds, which may also contain a carbonyl group and which may also be substituted by $C_1$ to $C_4$ alkyl, $C_1$ to $C_4$ halogenalkyl, optionally substituted aryl, and/or optionally substituted heteroaryl;

or; wherein R3 and R4 have the same meaning as above and wherein R5 and R6 together form a 5 or 6-membered ring which may optionally contain from 1 to 3 heteroatoms independently selected from the group consisting of: nitrogen, oxygen and sulfur and which may optionally bear 1 or 2 double bonds, which may also contain a carbonyl group and which may also be substituted by $C_1$ to $C_4$ alkyl, $C_1$ to $C_4$ halogenalkyl, optionally substituted aryl, and/or optionally substituted heteroaryl;

wherein Y—X is selected from the group consisting of: HC=CH, $CH_2$—$CH_2$, O=C—$CH_2$, and (HO)(H)C—$CH_2$;

and its physiologically compatible acid addition salts can be used for the treatment and/or inhibition of glaucoma, epilepsy, bipolar disorders, migraine, neuropathic pain, obesity, type II diabetes, metabolic syndrome, alcohol dependence, and/or cancer, and its concomitant and/or secondary diseases or conditions.

More specifically, in compounds of general Formula I R1 and R2 are independently selected from the group consisting of: hydrogen, $C_1$ to $C_4$ alkyl, $C_4$ to $C_7$ cycloalkyl, or wherein R1 and R2 together form a 5 or 6-membered ring which optionally may contain 1 or 2 heteroatoms independently selected from the group consisting of nitrogen and/or oxygen atoms and which may also be substituted by optionally substituted aryl, optionally substituted heteroaryl, or arylenehalogenalkyl; R3 to R6 are independently selected from the group consisting of: hydrogen, fluoro, chloro, bromo, methyl, ethyl, propyl, butyl, ethylene, propylene, methoxy, ethoxy, propoxy, ethinyl, propinyl, butinyl, $NH_2$, $NO_2$, $NSO_2CH_3$, aminomethyl, aminoethyl, aminopropyl, aminobutyl, aminodimethyl, aminodiethyl, aminodipropyl, aminodibutyl, cyano, oxyphenyl, oxybenzyl, oxyethylenephenyl, oxyphenylenemethyl, oxyphenylenemethoxy, acetyl, amidomethyl, amidoethyl, oxymethylenecarbonyl-methyl, oxyethylenecarbonylmethyl, oxymethylenecarbonylethyl, oxyethylenecarbonyl-ethyl, oxymethyleneoxymethyl, oxymethyleneoxyethyl, oxyethyleneoxymethyl, oxy-ethyleneoxyethyl, amidooxymethyl, and amidooxyethyl; and wherein Y—X is selected from the group consisting of: HC=CH, $CH_2$—$CH_2$, O=C—$CH_2$, and (HO)(H)C—$CH_2$.

Preferred compounds of Formula I according to the present invention are those in which R1 and R2 are both H, R3 to R6 are independently selected from the group consisting of hydrogen, halogen and $C_1$ to $C_4$ alkoxy; and Y—X is O=C—$CH_2$.

Other preferred compounds of Formula I according to the present invention are those in which R4 is selected from the group consisting of hydrogen, chlorine, bromine, and methoxy; and in which R5 is selected from the group consisting of hydrogen and bromine.

In another embodiment of the present invention, compounds of formula I are preferred in which R1 and R2 are independently selected from the group consisting of hydrogen, $C_1$ to $C_4$ alkyl, $C_4$ to $C_7$ cycloalkyl, or in which R1 and R2 together form a 5- or 6-membered ring which optionally may contain 1 or 2 heteroatoms independently selected from the group consisting of nitrogen and oxygen atoms and which may also be substituted by optionally substituted aryl, optionally substituted heteroaryl or arylenehalogenalkyl;

In which R3, R5 and R6 are independently selected from the group consisting of hydrogen; halogen; $C_1$ to $C_4$ alkyl; $C_2$ to $C_4$ alkenyl; $C_1$ to $C_4$ alkoxy; $C_1$ to $C_4$ alkoxy substituted with halogen, provided that the alpha-carbon atom is substituted by no halogen other than fluorine, if any; $C_2$ to $C_4$ alkinyl; $C_1$ to $C_4$ $NSO_2$alkyl; $NH_2$; $NO_2$; $C_1$ to $C_4$ aminoalkyl; $C_2$ to $C_8$ aminodialkyl; cyano; oxyaryl; oxyalkylenearyl; oxyarylenealkyl; oxyalkylenearylenealkoxy; $C_2$ to $C_8$ ester; $C_1$ to $C_8$ amido; $C_2$ to $C_8$ oxyalkylenecarbonylalkyl; $C_2$ to $C_8$ oxyalkyleneoxyalkyl; and $C_1$ to $C_4$ amidooxyalkyl; wherein R4 is selected from the group consisting of:
(a) phenyl, optionally substituted with one to three substituents independently selected from the group consisting of: hydrogen, amino, halogen, $C_1$ to $C_4$ alkyl, $C_1$ to $C_4$ alkoxy, oxyaryl, $C_1$ to $C_4$ mercapto, C(O)H, trifluoromethyl, —N—C(O)$C_{1-4}$alkyl, $C_2$ to $C_4$ alkenyl, C(O)$C_{1-4}$alkyl, and aryl;
(b) 1-naphthyl, 2-naphthyl, 2-pyridyl, 3-pyridyl, 4-pyridyl, 2-thiophenyl, 3-thiophenyl, quinoline, isoquinoline, benzo[b]thiophene, 1,3-dihydro-benzo[c]thiophene, 1-dibenzofuran, 2-dibenzofuran, 3-dibenzofuran, and 4-dibenzofuran, each optionally substituted with one to three substituents selected from the group consisting of: hydrogen, amino, halogen, $C_1$ to $C_4$ alkyl, $C_1$ to $C_4$ alkoxy, oxyaryl, C1 to C4 mercapto, C(O)H, trifluoromethyl, —N—C(O)$C_{1-4}$alkyl, $C_2$ to $C_4$ alkenyl, C(O)$C_{1-4}$alkyl, and aryl; and In which Y—X is selected from the group consisting of HC=CH, $CH_2$—$CH_2$, O=C—$CH_2$, and (HO)(H)C—$CH_2$.

More preferred are compounds in which R1, R2, R3, R5 and R6 are all hydrogen; and in which R4 is selected from the group consisting of:
(a) phenyl optionally substituted with one to three substituents independently selected from the group consisting of: hydrogen, amino, halogen, $C_1$ to $C_4$ alkyl, $C_1$ to $C_4$ alkoxy, oxyaryl, C1 to C4 mercapto, C(O)H, trifluoromethyl, —N—C(O)$C_{1-4}$alkyl, C2 to C4 alkenyl, C(O)$C_{1-4}$alkyl, aryl;
(b) 1-naphthyl, 2-naphthyl, 2-pyridyl, 3-pyridyl, 4-pyridyl, 2-thiophenyl, 3-thiophenyl, quinoline, isoquinoline, benzo[b]thiophene, 1,3-dihydro-benzo[c]thiophene, 1-dibenzofuran, 2-dibenzofuran, 3-dibenzofuran, 4-dibenzofuran; and In which Y—X is O=C—$CH_2$.

Wherever the compounds of the present invention or other compounds described within the context of the present invention substituents are or contain $C_1$ to $C_4$-alkyl, $C_2$ to $C_4$-alkenyl, $C_1$ to $C_4$-alkoxy, $C_1$ to $C_4$-alkoxy substituted with halogen provided that the alpha-carbon atom is substituted by no halogen other than fluorine if any, $C_2$ to $C_4$-alkinyl, aminoalkyl, $C_2$ to $C_8$ dialkyl, oxyaryl, oxyalkylenearyl, oxyarylenealkyl, oxyalkylenearylenealkoxy, $C_2$ to $C_8$ ester, $C_1$ to $C_8$ amido, $C_2$ to $C_8$ oxyalkylenecarbonylalkyl, $C_2$ to $C_8$ oxyalkyleneoxyalkyl, or $C_1$ to $C_4$ amidooxyalkyl, these may each be straight-chain or branched. If substituents in compounds of Formula I represent halogen, fluorine, chlorine, bromine or iodine are suitable. Chlorine and bromine are preferred.

Aryl and/or arylene preferably stands for phenyl and phenylene. Where aryl and/or arylene is optionally substituted, the phenyl or phenylene may be substituted with one to three substituents independently selected from the group consisting of hydrogen, amino, halogen, $C_1$ to $C_4$ alkyl, $C_1$ to $C_4$ alkoxy, oxyaryl, $C_1$ to $C_4$ mercapto, C(O)H, trifluoromethyl, —N—C(O)$C_{1-4}$alkyl, $C_2$ to $C_4$ alkenyl, C(O)$C_{1-4}$alkyl, aryl, cyano, nitro, and $C_1$ to $C_4$ alkylsulfonyl. More preferred are halogen, $C_1$ to $C_4$ alkyl, $C_1$ to $C_4$ alkoxy and trifluoromethyl. Unsubstituted phenyl is also an alternative.

Heteroaryl preferably stands for pyridyl and pyridylene, in particular 2-pyridyl, 3-pyridyl or 4-pyridyl; pyrimidinyl and pyrimidinylene, in particular 2-pyrimidinyl, 5-pyrimidinyl, 2-pyrimidinylene and 5-pyrimidinylene; oxazolyl; thiazolyl; thiophenyl, in particular 2-thiphenyl, 3-thiophenyl; and furanyl, in particular, 2-furanyl and 3-furanyl. Phenyl, pyridyl and pyrimidinyl are more preferred. Where heteroaryl is optionally substituted, it is substituted with halogen, trifluoromethyl, cyano, $C_1$ to $C_4$ alkyl or $C_1$ to $C_4$ alkoxy.

Condensed aryl and condensed heteroaryl denote naphthyl, in particular 1-naphthyl, 2-naphthyl; quinolinyl; isoquinolinyl; 1,2,3,4-tetrahydroisoquinolinyl; indoly; isoindolinyl; benzo[b]thiophene, 1,3-dihydro-benzo[c]thiophene, 1-dibenzofuran, 2-dibenzofuran, 3-dibenzofuran, 4-dibenzofuran. Where condensed aryl or heteroaryl is optionally substituted, it is substituted with halogen, trifluoromethyl, cyano, $C_1$ to $C_4$ alkyl or $C_1$ to $C_4$ alkoxy.

Physiologically compatible acid addition salts of compounds of Formula I are their conventional salts with inorganic acids, for example sulfuric acid, phosphoric acids or hydrohalic acids, preferably hydrochloric acid, or with organic acids, for example lower aliphatic monocarboxylic, dicarboxylic or tricarboxylic acids such as maleic acid, fumaric acid, lactic acid, tartaric acid, citric acid, or with sulfonic acids, for example lower alkanesulfonic acids such as methanesulfonic acid or trifluoromethanesulfonic acid, or benzenesulfonic acids optionally substituted in the benzene ring by halogen or lower alkyl, such as p-toluenesulfonic acid. Hydrochloric acid salts of the compounds of general Formula I are preferred.

In general, compounds of Formula I can be prepared by reacting a benzopyran compound of Formula II,

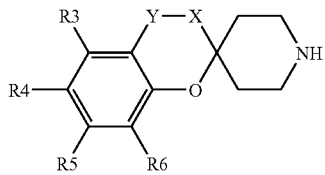

II

In which R3 to R6, X and Y have the above meanings, with sulfamide, or, with a sulfamoylchloride, which is optionally protected with a protecting group, preferably tert.-butyloxycarbonyl, corresponding to Formula IV,

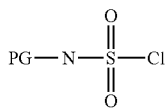

IV and if desired converting resulting free bases of Formula I into their physiologically acceptable salts, or converting salts of the compounds of Formula I into the free bases of Formula I.

Compounds of Formula I can also be produced by reacting a benzopyran corresponding to Formula II

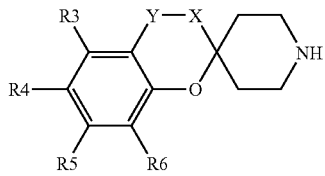

II

In which R3 to R6, X and Y have the above meanings, with a compound of Formula III

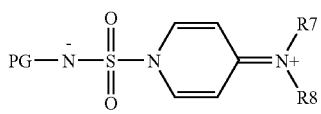

III

In which R7 and R8 represent $C_1$ to $C_6$ alkyl and/or $C_3$ to $C_8$ cycloalkyl, and PG is a protecting group, preferably tert.-butyloxycarbonyl, and subsequently cleaving off the protecting group under suitable, preferably acidic, conditions from the obtained intermediate compound, and if desired converting resulting free bases of Formula I into their physiologically acceptable acid addition salts, or converting the acid addition salts of the compounds of Formula I into the free bases of Formula I. In a preferred embodiment of this process, R7 and R8 are both methyl.

Compounds of Formula I in which R1 and R2 are not hydrogen can be produced by reacting a benzopyran of Formula II

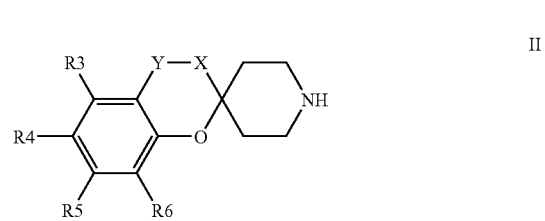

II

In which R3 to R6, X and Y have the above meanings, with a sulfamoylchloride, which is preferably protected with a protecting group, preferably tert.-butyloxycarbonyl, of Formula IV,

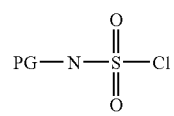

IV and subsequently cleaving off the protecting group under suitable, preferably acidic, conditions from the obtained intermediate product, and if desired converting resulting free bases of Formula I into their physiologically acceptable acid addition salts, or converting the acid addition salts of the compounds of Formula I into the free bases of Formula I.

Compounds of Formula I in which R1 and R2 are not hydrogen can be produced by reacting a benzopyran of Formula II

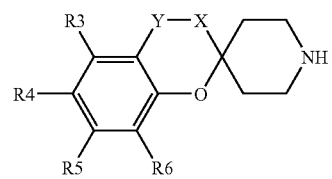

II

In which R3 to R6, X and Y have the above meanings, with a sulfamoylchloride of Formula IVa,

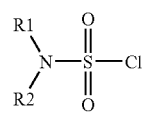

IVa

In which R1 and R2 have the above meanings, and if desired converting the resulting free bases of Formula I into their physiologically acceptable acid addition salts, or converting the acid addition salts of the compounds of Formula I into the free bases of Formula I.

Compounds of Formula I in which at least one of R3 to R6 is optionally substituted aryl; optionally substituted heteroaryl; optionally substituted condensed aryl, or optionally substituted condensed heteroaryl, can be prepared by reacting a compound of Formula I in which at least one of R3 to R6 is bromo, chloro, or, iodo, preferably bromo or chloro, more preferably bromo, with a compound of formula IX

W—B(OH)$_2$      IX in which W is selected from the group consisting of optionally substituted aryl, optionally substituted heteroaryl; optionally substituted condensed aryl, and optionally substituted condensed heteroaryl. This reaction requires the presence of palladium(0) (generated, for example from palladium-(II)-acetate) and a phosphine ligand, e.g., a biphenyl phosphane catalyst as disclosed in Buchwald et al., Angew. Chem. Int. Ed., 2004, 43, 1871-1876. Examples of suitable catalysts include any of the following:
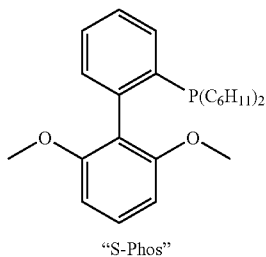
"S-Phos"
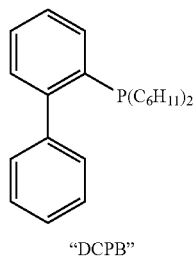
"DCPB"
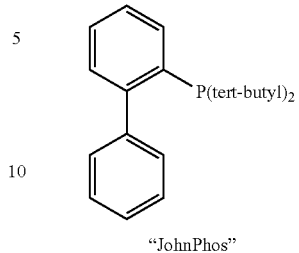
"JohnPhos"
More specifically, compounds of Formula I can be produced as follows:
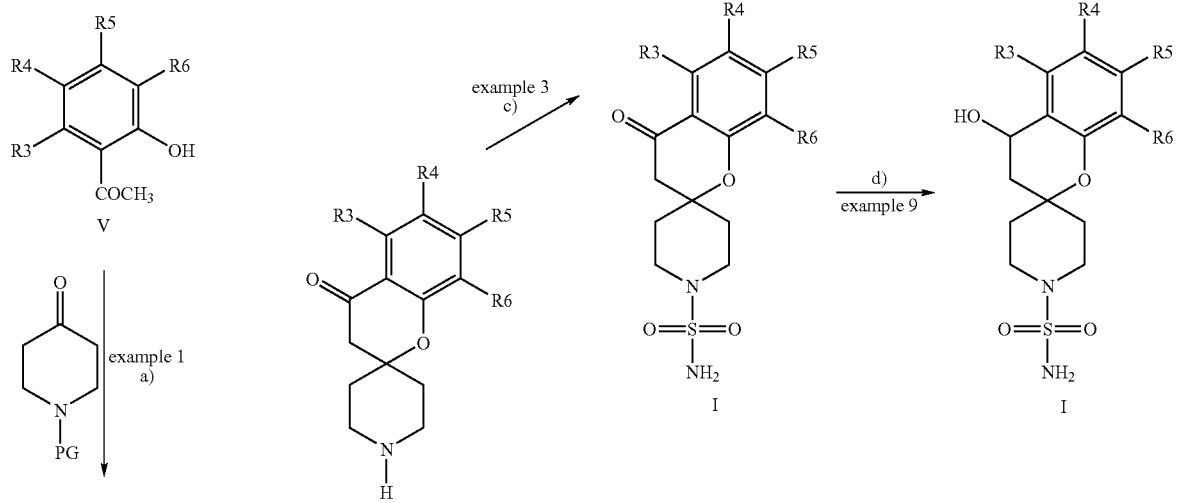
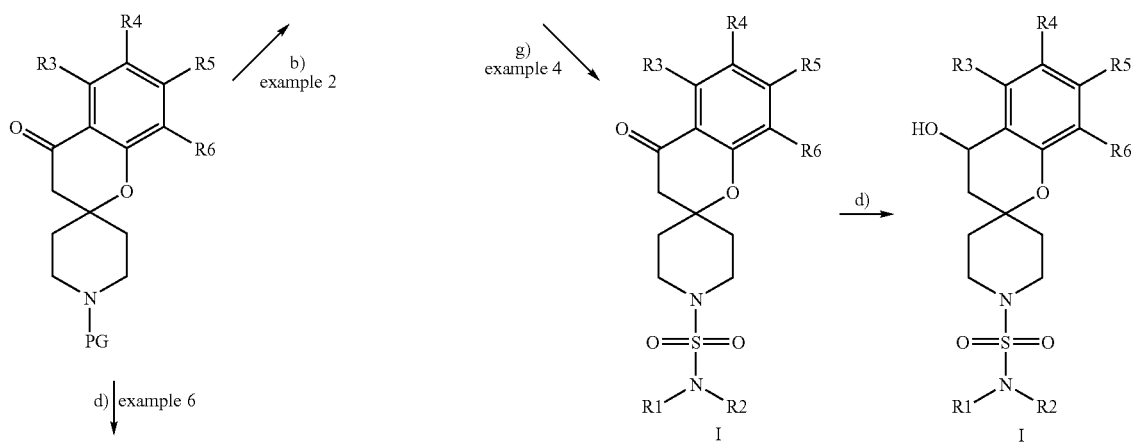

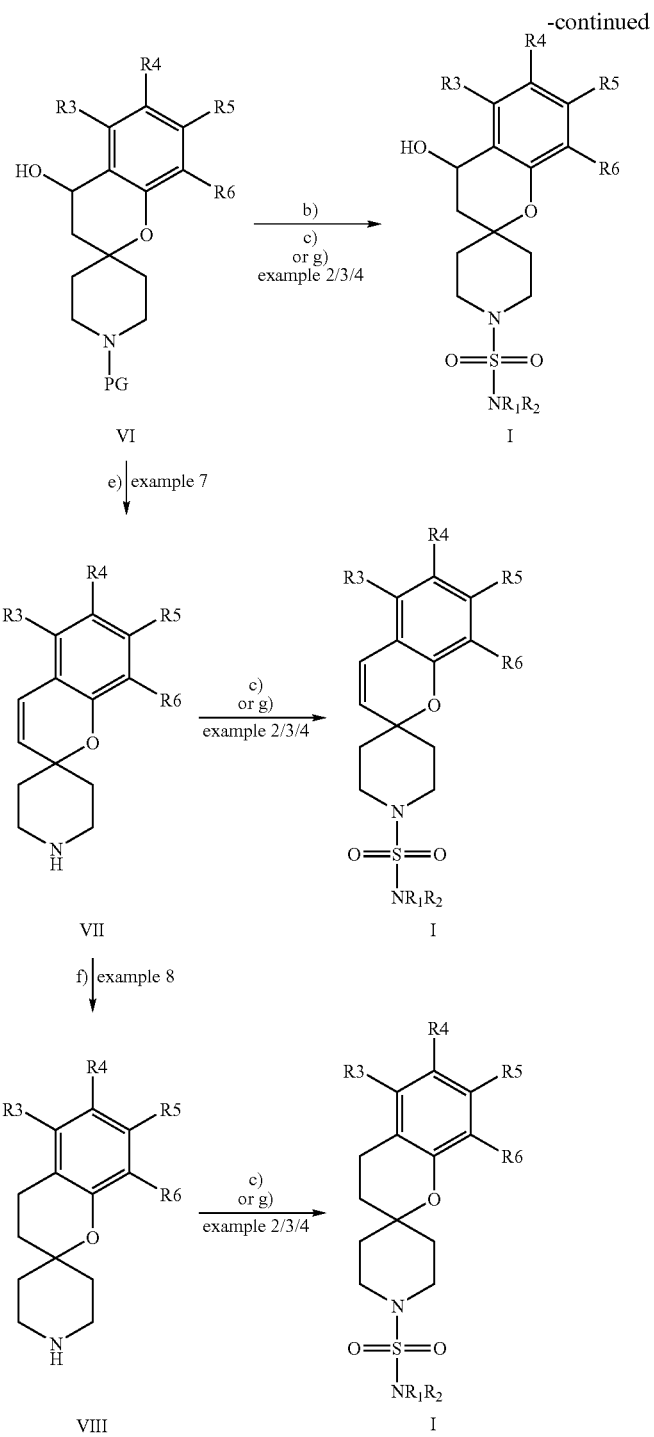

and if desired converting resulting free bases of Formula I into their physiologically acceptable salts, or converting salts of the compounds of Formula I into the free bases of Formula I.

Any compound of Formula I obtained by any process as described in the scheme above can be further reacted to the give a compound of Formula I in which any of R3 to R6 is represented by optionally substituted aryl, optionally substituted heteroaryl, optionally substituted condensed aryl, or optionally substituted condensed heteroaryl.

In process step a), the reaction can be carried out in an organic solvent which is inert under the reaction conditions, in particular in a solvent such as methanol. Suitable reaction temperatures are between room temperature and the boiling point of the solvent, preferably between 30° C. and 65° C. The crude product can optionally be purified on a suitable gel, e.g., silica gel, if needed to obtain the spiro compound in good yield.

In process step b), the protecting group, preferably tert.-butyloxycarbonyl, can subsequently be cleaved off in a known manner in acidic media, e.g. in an ethanolic solution of hydrochloric acid or even with concentrated hypochloric acid. The yield can be optimized by extracting the crude reaction mixture with a dipolar-aprotic solvent such as chloroform, dichloromethane or a mixture of such solvents.

In process step c), the reaction can be carried out in an organic solvent which is inert under the reaction conditions, in particular in an aprotic solvent such as toluene or xylene or in a mixture of such solvents. Suitable reaction temperatures are between room temperature and the boiling point of the solvent or solvent mixture, preferably between 60° C. and 100° C. After cooling to room temperature, the solvents are evaporated and the remaining solids dissolved in an organic inorganic solvent mixture such as methanol, tetrahydrofuran and water. Removal of the solvents leads to compounds of Formula I in good yield.

In process step d), the reaction can be carried out in an organic solvent which is inert under the reaction conditions, in particular in a protic solvent such as methanol or ethanol or in a mixture of such solvents. Suitable reaction temperatures are between 0° C. and room temperature, preferably between 10° C. and 20° C. The solvents are evaporated and the remaining solids dissolved in an organic/inorganic solvent mixture such as ethyl acetate and water. Removal of the solvents leads to compounds of Formula VI in good yield.

In process step e), the reaction can be carried out in an organic solvent which is inert under the reaction conditions, in particular in an aprotic solvent such as toluene or xylene or in a mixture of such solvents. Suitable reaction temperatures are between room temperature and the boiling point of the solvent or solvent mixture, preferably between 60° C. and 100° C. After cooling to room temperature, the solvents are evaporated and the remaining solids dissolved in an organic inorganic solvent mixture such as ethyl acetate and water. Removal of the solvents leads to compounds of Formula VII in good yield.

In process step f), the reaction can be carried out in an organic solvent which is inert under the reaction conditions, in particular in a protic solvent such as methanol or ethanol or in a mixture of such solvents. Suitable reaction temperatures are between room temperature and the boiling point of the solvent or solvent mixture, preferably between 20° C. and 40° C. After cooling to room temperature, the solvents are evaporated and the remaining solids dissolved in an organic inorganic solvent mixture such as ethyl acetate and water. Removal of the solvents leads to compounds of Formula VIII in good yield.

In process step g) the benzopyran derivative is reacted with the respective sulfamoylchloride in an inert organic solvent, e.g., dichloromethane or THF, preferably in the presence of a base, e.g., triethylamine. In a preferred embodiment, the benzopyran is used in excess. To remove excess or reagents, polymeric isocyanate and trisamine can be added.

Starting materials, such as compounds of Formula V:

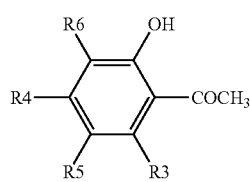

for the above reaction pathways are either commercially available, or can be prepared by one of the reaction pathways described in the following examples.

1. Para-anisidine was acylated at the amino center with acetic anhydride in dichloromethane and the product was obtained in 91% yield. Then, Friedel Craft's acylation was carried out with acetyl chloride in the presence of anhydrous aluminum chloride in dichloromethane to obtain the hydroxyl acetophenone in 70% yield. Nitration of acetanilide derivative was carried out with nitric acid in aqueous acetic acid to get the product in 45% yield. The acetyl group of acetamido functionality was removed by refluxing in dilute hydrochloric acid for 2.5 hours to obtain the aniline derivative in quantitative yield. Deamination was done by diazotization and treating the diazonium salt with ethanol to obtain the 3-nitro-2-hydroxyacetophenone. The nitro group was reduced by heating the reaction mixture in ethyl acetate with tin in hydrochloric acid resulting in the formation of corresponding amino compound. Lastly, the Sandemeyer reaction was carried out to obtain the desired bromo derivative Va in 25% yield.

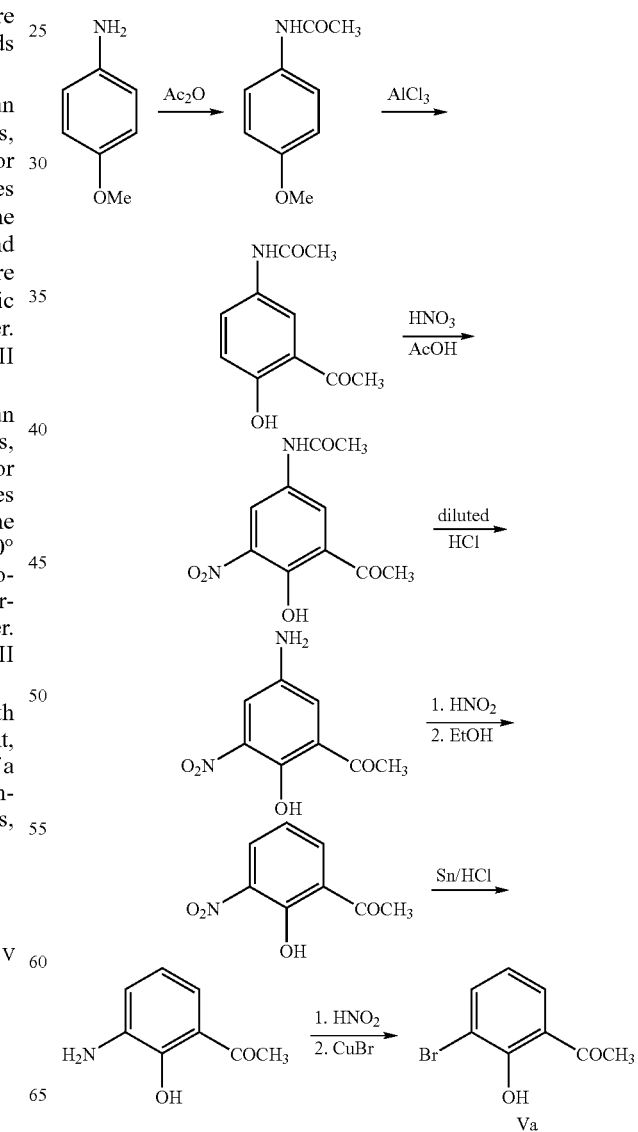

2. 2-hydroxy-4-bromoacetophenone was synthesized through the schematic pathway shown below. 3-bromophenol was acylated with acetic anhydride in the presence of catalytic quantity of sulfuric acid to obtain the acylated product in quantitative yield. Fries migration of the same was carried out by heating with anhydrous aluminum chloride in o-dichlorobenzene for 8 hours to obtain the product in 70% yield, which was condensed with N-bocpiperidone in methanol in the presence of pyrrolidine, and desired product Vb was obtained in 65% yield.

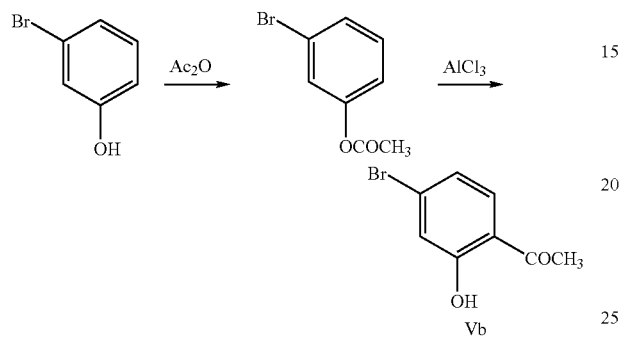

3. 2-hydroxy-5-cyanoacetophenone was obtained by acylation of 3-cyanophenol and carrying out Fries Migration. Acylation was achieved by treating the cyanophenol with acetic anhydride in the presence of a catalytic amount of concentrated sulfuric acid leading to 59% of the pure acetylated product. Further, the phenyl acetate was subjected to Fries Migration conditions, i.e, by heating at 180-185° C. with aluminum chloride for 3 hours, and the desired product Vc was isolated in 45% yield.

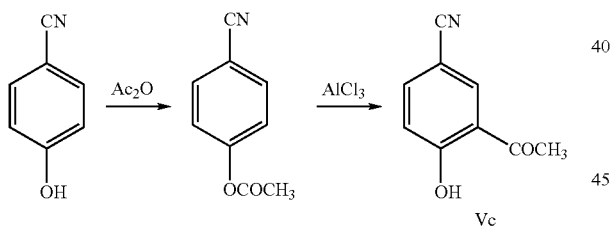

4. 4-amino-2-hydroxyacetophenone was obtained through the pathway given below. 3-Aminophenol was used as the raw material and condensed with acetic anhydride in the presence of pyridine to obtain the diacetyl derivative in 80% yield. Fries migration was carried out with this compound by heating with anhydrous aluminum chloride at 170-180° C. for 8 hours to obtain the acetophenone derivative, which was hydrolyzed without isolation by refluxing in 2N HCl to obtain the product Vd in 60% yield.

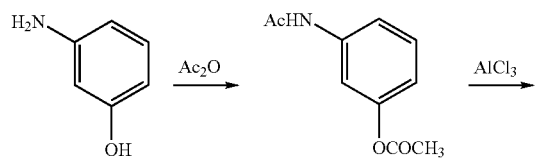

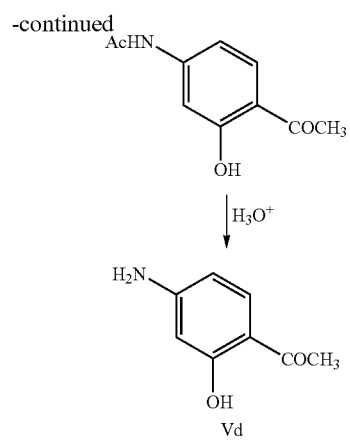

5. p-Anisidine was acylated at the amino center with acetic anhydride in dichloromethane, and the acylated product was obtained in 91% yield . Then, Friedel Craft's acylation was carried out with acetyl chloride in the presence of anhydrous aluminium chloride in DCM to obtain the hydroxyacetophenone derivative. The intermediate was isolated in 70% yield. 5-Acetamido-2-hydroxyacetophenone was hydrolyzed in 2N hydrochloric solution by refluxing for 6 hours, yielding 94% of 5-amino-2-hydroxyacetophenone.

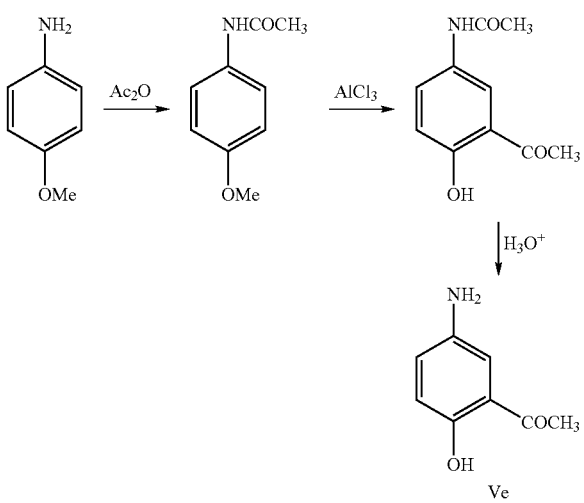

Other compounds of general Formula V can be prepared in a similar manner by replacing the starting materials respectively.

In yet another aspect, the present invention also relates to a method of treating or inhibiting of glaucoma, epilepsy, bipolar disorders, migraine, neuropathic pain, obesity, type II diabetes, metabolic syndrome, alcohol dependence, and/or cancer, and associated concomitant and/or secondary diseases or conditions in mammals and humans, comprising administering to a subject in need thereof a therapeutically effective amount of a compound of Formula I or a physiologically compatible acid addition salt thereof.

Obesity according to the present invention is meant to comprise any increase in body fat that results in increased bodyweight, comprising as a preferred alternative but not limited to the medical definition of obesity. The invention thus also relates to non-medical weight loss, such as cosmetic weight loss and includes improving bodily appearance in general. Further, the term obesity also is meant to comprise drug induced obesity and/or juvenile obesity.

The concomitant diseases of obesity and its concomitant and/or secondary diseases or conditions in mammals and humans according to the invention include in particular the metabolic syndrome and/or syndrome X and cardiovascular diseases.

The term "metabolic syndrome" as used in this application is meant to cover a complex of clinical pictures which—besides central obesity—mainly comprises hypertension, in particular arterial hypertension; insulin resistance, in particular diabetes mellitus type II; glucose intolerance; dyslipoproteinaemia, in particular as hypertriglyceridaemia, accompanied by dyslipoproteinaemia occurring with lowered HDL-cholesterol, and also hyperuricaemia, which can lead to gout. According to information from the American Heart Association, the metabolic syndrome is closely linked to insulin resistance. Some people are genetically predisposed to insulin resistance. Acquired factors, such as excess body fat and physical inactivity, can elicit insulin resistance and the metabolic syndrome in these people. Most people with insulin resistance have central obesity. The biologic mechanisms at the molecular level between insulin resistance and metabolic risk factors are not fully understood and appear to be complex. One group of people at risk for developing metabolic syndrome are those with diabetes who have a defect in insulin action and cannot maintain a proper level of glucose in their blood. Another risk group is people, mainly those with high blood pressure, who are nondiabetic and insulin-resistant but who compensate by secreting large amounts of insulin. This condition is known as hyperinsulinemia. A third group is heart attack survivors who, unlike hypertensives, have hyperinsulinemia without having abnormal glucose levels. The metabolic syndrome has become increasingly common in more developed countries like the United States, where it is estimated that about 20-25 percent of US adults have it. There are no well-accepted criteria for diagnosing the metabolic syndrome. The criteria proposed by the Third Report of the National Cholesterol Education Program (NCEP) Expert Panel on Detection, Evaluation, and Treatment of High Blood Cholesterol in Adults (Adult Treatment Panel III) are the most current and widely used. According to the ATP III criteria, the metabolic syndrome is identified by the presence of three or more of these components:

Central obesity as measured by waist circumference (Men—Greater than 40 inches; Women—Greater than 35 inches).

Fasting blood triglycerides greater than or equal to 150 mg/dL.

Blood HDL cholesterol (Men—Less than 40 mg/dL; Women—Less than 50 mg/dL)

Blood pressure greater than or equal to 130/85 mmHg.

Fasting glucose greater than or equal to 110 mg/dL.

The term "syndrome X" is closely related to the term "metabolic syndrome" and usually is supposed to denominate the identical disease or condition. According to information from the American Heart Association, the term "Syndrome X" refers, however, additionally to a heart condition where chest pain and electrocardiographic changes that suggest ischemic heart disease are present, but where there are no angiographic findings of coronary disease. Patients with cardiac syndrome X also sometimes have lipid abnormalities.

The term "cardiovascular diseases" in conjunction with obesity is usually understood to mean coronary heart disease, which can lead to heart failure, cerebrovascular diseases, which may for example be accompanied by an increased risk of strokes, and peripheral occlusive arterial disease.

Due to their inherent properties, the compounds of Formula I or their physiologically compatible acid addition salts are also expected to be useful in the treatment of diabetic conditions or diseases which are unrelated to obesity. Such diabetic conditions or diseases comprise e.g. diabetes mellitus type II, diabetic neuropathy, diabetic retinopathy, diabetic nephropathy, diabetic microangiopathy or diabetic macroangiopathy.

Further concomitant and/or secondary diseases of obesity include gall-bladder diseases such as formation of gallstones, sleep apnea syndrome, orthopedic complications such as osteoarthritis and psychosocial disorders.

The compounds of Formula I are further deemed to be useful as anticonvulsants for the inhibition or treatment of epilepsy in mammals and humans.

The compounds of Formula I according to the invention are inhibitors of mammalian carbonic anhydrases, in particular of human carbonic anhydrase isozymes of subtypes II and/or V (=hCA II and/or hCA V).

Pharmacological Test Methods

The example numbers quoted in the pharmacological test methods relate to the following preparation examples.

1. In vitro Inhibition of Human Carbonic Anhydrase Isoenzyme II (hCA II)

The test compounds of general Formula I in 96 well microplates were diluted with aqua bidest by using an automatic pipettor (CyBiWell®). From the different dilution plates, aliquots of 20 µl were transferred to the 96 well black assay plates with a pipetting station (Tecan Genesis®). In a second step, 148 µl of potassium phosphate buffer (20 mM, pH 7.4) was added, and as a third step, 20 µl of enzyme solution (1 µM human carbonic anhydrase isoenzyme II from erythrocytes (Sigma-Aldrich), dissolved in potassium phosphate buffer) incubated for 60 min at room temperature and the fluorescence signal (Tecan Ultra® fluorescence reader; excitation wavelength: 280 nm; emission wavelength: 465 nm) read at the end of the preincubation period (FLU-1). After the preincubation time, 20 µl of aqueous dansylamide solution (1 mM dansylamide (Sigma-Aldrich), dissolved in hydrochloric acid) were added and the fluorescence signal read every 10 min for a period of 60 min at 37° C. For calculation, the fluorescence data of the time point 60 min (FLU-2) were used. The total volume of assay mixture amounted to 208 µl. The final concentration of carbonic anhydrase II was $10^{-7}$ M/L, of dansylamide $2.25 \times 10^{-6}$ and of compounds from $10^{-8}$ M/L up to $10^{-5}$ M/L. Final concentration of DMSO as compound solvent was 0.1 mM. Each microplate also contained blanks without compound and enzyme, controls without compound and ethoxzolamide (final concentration $5 \times 10^{-8}$ M/L). All data reflect single measurements. Data were expressed as % inhibition after calculation by the formula:

% inhibition=$100((1-(\text{FLU-2}_{cpd}-\text{FLU-2}_{blank}-\text{FLU-1}_{cpd}+\text{FLU-1}_{blank})/(\text{FLU-2}_{control}-\text{FLU-2}_{blank}-\text{FLU-1}_{control}-\text{FLU-1}_{blank}))$ The % inhibition data for each compound and the respective final concentrations were used for $IC_{50}$ calculations by using the Prism 4 software. Concentration action figures were calculated by applying the Prism algorithm for nonlinear regression (curve-fit): sigmoidal dose response with variable slope and the constraints: top: 100 and bottom 0.

In this test model, the test substances of general Formula I listed in Table 1 below showed the $IC_{50}$ values given below:

TABLE 1

| hCA II inhibiting effect of the test substances in vitro | |
|---|---|
| Example No. | $IC_{50}$ [µM] |
| 1 | 6.6 |
| 2 | 6.6 |
| 3 | 7.7 |
| 4 | 6.4 |

2. Acute in vivo Food Intake Test in Mice

The studies were carried out in male or female C57Bl/6 mice (n=8-12 per group). The mice were kept on an inverted 12/12 h light/dark cycle (lights on 22:00). They were allowed food (high caloric diet) and water ad libitum. Food intake and water consumption was measured daily. The test compound of general Formula I was suspended in 1% methylcellulose in water and 2% (v/v) of Poloxamer 188 (Lutrol F68®) and administered by oral gavage at a dose of 100 mg/kg/day. One half of the dose was administered at 7.00-9.00 h; the remaining half of the dose was administered between 15.00-15.30 h.

In the test model described above, the test substances caused a decrease of the animals' 24 h food intake to the percentages of food intake when compared to control as given in the following Table 2.

TABLE 2

| Influence of test substances on food intake | |
|---|---|
| Example No. | food intake [% of control] |
| 1 | 83 |

The present invention further provides a pharmaceutical composition or medicament comprising a pharmacologically effective quantity of a compound of general Formula I or its physiologically compatible acid addition salts and further comprising conventional pharmaceutically acceptable auxiliaries and/or carriers.

Suitable pharmaceutically acceptable auxiliaries and/or carriers are well known in the art and include pharmaceutical grade starch, mannitol, lactose, magnesium stearate, sodium saccharin, talcum, cellulose, glucose, sucrose (or other sugar), magnesium carbonate, gelatin, oil, alcohol, detergents, emulsifiers or water (preferably sterile). The composition may be a mixed preparation of a composition or may be a combined preparation for simultaneous, separate or sequential use (including administration). The compounds according to the invention or their physiologically compatible acid addition salts for use in the aforementioned indications may be administered by any convenient method, for example by oral (including by inhalation), parenteral, mucosal (e.g. buccal, sublingual, nasal), rectal or transdermal administration and the compositions adapted accordingly. For oral administration, the compounds can be formulated as liquids or solids, for example solutions, syrups, suspensions or emulsions, tablets, capsules and lozenges. A liquid formulation will generally consist of a suspension or solution of the compound or physiologically acceptable salt in a suitable aqueous or non-aqueous liquid carrier(s) for example water, ethanol, glycerine, polyethylene glycol or an oil.

The formulation may also contain a suspending agent, preservative, flavoring or coloring agent. A composition in the form of a tablet can be prepared using any suitable pharmaceutical carrier(s) routinely used for preparing solid formulations. Examples of such carriers include magnesium stearate, starch, lactose, sucrose and microcrystalline cellulose. A composition in the form of a capsule can be prepared using routine encapsulation procedures. For example, powders, granules or pellets containing the active ingredient can be prepared using standard carriers and then filled into a hard gelatin capsule; alternatively, a dispersion or suspension can be prepared using any suitable pharmaceutical carrier(s), for example aqueous gums, celluloses, silicates or oils and the dispersion or suspension then filled into a soft gelatin capsule. Compositions for oral administration may be designed to protect the active ingredient against degradation as it passes through the alimentary tract, for example by an outer coating of the formulation on a tablet or capsule. Typical parenteral compositions consist of a solution or suspension of the compound or physiologically compatible acid addition salts in a sterile aqueous or non-aqueous carrier or parenterally acceptable oil, for example polyethylene glycol, polyvinyl pyrrolidone, lecithin, arachis oil or sesame oil. Alternatively, the solution can be lyophilised and then reconstituted with a suitable solvent just prior to administration. Compositions for nasal or oral administration may conveniently be formulated as aerosols, drops, gels and powders.

Aerosol formulations typically comprise a solution or fine suspension of the active substance in a physiologically acceptable aqueous or non-aqueous solvent and are usually presented in single or multidose quantities in sterile form in a sealed container, which can take the form of a cartridge or refill for use with an atomising device. Alternatively the sealed container may be a unitary dispensing device such as a single dose nasal inhaler or an aerosol dispenser fitted with a metering valve which is intended for disposal once the contents of the container have been exhausted. Where the dosage form comprises an aerosol dispenser, it will contain a pharmaceutically acceptable propellant. The aerosol dosage forms can also take the form of a pump-atomiser. Compositions suitable for buccal or sublingual administration include tablets, lozenges and pastilles, wherein the active ingredient is formulated with a carrier such as sugar and acacia, tragacanth, or gelatin and glycerin. Compositions for rectal or vaginal administration are conveniently in the form of suppositories (containing a conventional suppository base such as cocoa butter), pessaries, vaginal tabs, foams or enemas. Compositions suitable for transdermal administration include ointments, gels, patches and injections including powder injections. Conveniently the composition is in unit dose form such as a tablet, capsule or ampoule. The pharmaceutical compositions according to the invention are useful in the treatment and/or prophylaxis and/or prevention of glaucoma, epilepsy, bipolar disorders, migraine, neuropathic pain, obesity, type II diabetes, metabolic syndrome, alcohol dependence, and/or cancer, and its concomitant and/or secondary diseases or conditions; other medical weight loss and non-medical related weight loss; and/or diabetic conditions or diseases.

The compounds of the present invention and their physiologically compatible acid addition salts are generally administered as pharmaceutical compositions which are important and novel embodiments of the invention because of the presence of the compounds disclosed herein. In embodiments of the invention, a pharmaceutical pack or kit is provided comprising one or more container(s) filled with one or more of the ingredients of a pharmaceutical composition of the invention. Associated with such container(s) can be various written materials such as instructions for use, or a notice in the form prescribed by a governmental agency regulating the manufacture, use or sale of pharmaceuticals products, which notice reflects approval by the agency of manufacture, use, or sale for human or veterinary administration.

Yet a further aspect of the invention provides a process for the manufacture of a pharmaceutical composition as described above. The manufacture can be carried out by standard techniques well known in the art and involves combining a compound according to the invention and the pharmaceutically acceptable auxiliaries and/or carriers. The composition may be in any form including a tablet, a liquid, a capsule, and a powder or in the form of a food product, e.g. a functional food. In the latter case the food product itself may act as the pharmaceutically acceptable carrier.

The compound or composition is preferably administered to a patient in need thereof and in a quantity sufficient to prevent and/or treat the symptoms of the condition, disorder or disease. For all aspects of the invention, particularly medical ones, the administration of a compound or composition has a dosage regime which will ultimately be determined by the attending physician and will take into consideration such factors such as the compound being used, animal type, age, weight, severity of symptoms, method of administration, adverse reactions and/or other contraindications. Specific defined dosage ranges can be determined by standard design clinical trials with patient progress and recovery being fully monitored. Such trials may use an escalating dose design using a low percentage of the maximum tolerated dose in animals as the starting dose in man. The physiologically acceptable compounds of the invention will normally be administered in a daily dosage regimen (for an adult patient) of, for example, an oral dose of between 1 mg and 2000 mg, preferably between 30 mg and 1000 mg, e.g. between 10 and 250 mg or an intravenous, subcutaneous, or intramuscular dose of between 0.1 mg and 100 mg, preferably between 0.1 mg and 50 mg, e.g. between 1 and 25 mg of the compound of the general Formula I or a physiologically acceptable salt thereof calculated as the free base, the compound being administered 1 to 4 times per day. The compound used according to the invention can also be administered to children or juveniles while the individual dosage regimens in these cases will need to be particularly thoroughly adjusted by the physician and will usually comprise lower doses than will be administered to adults.

Suitably, the compounds will be administered for a period of continuous therapy, for example for at least a week, but usually for a longer period of several weeks to several months. The invention also provides a cosmetic method (non-therapeutic) for maintaining a given weight, or for cosmetic weight loss, the method comprising the administration of a compound according to the other aspects of the invention, preferably in combination with a pharmaceutically acceptable carrier or diluent.

The compound or composition is preferably administered to a subject in need or in desideratum thereof and in a quantity sufficient to maintain a given weight or for cosmetic weight loss.

In still a further aspect, the compounds of Formula I and their physiologically compatible acid addition salts may be administered advantageously in combination with one or more active agents (as a pharmaceutical combination composition) selected from antidiabetics; antiobesity or appetite-regulating agents; cardiovascular active agents, in particular antihypertensives; diuretics; active agents altering lipid levels, in particular lipid-lowering agents; and active ingredients for the treatment and/or inhibition of complications caused by diabetes or associated with diabetes.

Suitable antidiabetics comprise e.g. insulins, amylin, derivatives of GLP-1 and GLP-2 such as, for example, those disclosed in U.S. Pat. No. 6,268,343 (=WO 98/08871) and orally active hypoglycemic active ingredients. The orally active hypoglycemic active ingredients preferably comprise sulfonylureas, e.g tolbutamide, glibenclamide, glimepiride, glipizide, gliquidone, glisoxepide, glibomuride or gliclazide; biguanides, e.g. metformin; meglitinides, e.g. repaglinide; beta3 adrenergic agonists; oxadiazolidinediones; glucosidase inhibitors e.g. alpha-glucosidase inhibitors such as miglitol or acarbose; glucagon receptor antagonists, GLP-1 agonists, potassium channel openers like diazoxide or those disclosed in U.S. Pat. No. 5,889,002 or U.S. Pat. No. 6,225,310 (=WO 97/26265 or WO 99/03861); CB-1 (cannabinoid-1 receptor) antagonists/inverse agonists; insulin sensitizers like thiazolidinediones, e.g. troglitazone, ciglitazone, pioglitazone, rosiglitazone or the compounds disclosed in U.S. Pat. No. 5,885,997 (=WO 97/41097, in particular 5-[[4-[(3,4-dihydro-3-methyl4-oxo-2-quinazolinylmethoxy]-phenyl]methyl]-2, 4-thiazolidinedione; activators of insulin receptor kinase; inhibitors of liver enzymes involved in the stimulation of gluconeogenesis and/or glycogenolysis, for example inhibitors of glycogen phosphorylase; and modulators of glucose uptake and glucose excretion.

Suitable antiobesity or appetite-regulating agents comprise one or more of a 5-HT (serotonin) transporter inhibitor, a NE (norepinephrine) transporter inhibitor, a CB-1 (cannabinoid-1 receptor) antagonist/inverse agonist, a ghrelin antibody, a ghrelin antagonist, a H3 (histamine H3) antagonist/inverse agonist, a MCH1R (melanin concentrating hormone 1R) antagonist, a MCH2R (melanin concentrating hormone 2R) agonist/antagonist, a NPY1 (neuropeptide Y Y1) antagonist, a NPY2 (neuropeptide Y Y2) agonist, a NPY5 (neuropeptide Y Y5) antagonist, leptin, a leptin derivative, an opioid antagonist, an orexin antagonist, a BRS3 (bombesin receptor subtype 3) agonist, a CCK-A (cholecystokinin-A) agonist, a CNTF (ciliary neurotrophic factor), a CNTF derivative, a GHS (growth hormone secretagogue receptor) agonist, SHT2c (serotonin receptor 2c) agonist, a Mc3r (melanocortin 3 receptor) agonist, a Mc4r (melanocortin 4 receptor) agonist, a monoamine reuptake inhibitor, a serotonin reuptake inhibitor, a GLP-1 (glucagon-like peptide 1) agonist, topiramate, phytopharm compound 57, an ACC2 (acetyl-CoA carboxylase-2) inhibitor, a beta3 adrenergic agonist, a DGAT1 (diacylglycerol acyltransferase 1) inhibitor, a DGAT2 (diacylglycerol acyltransferase 2) inhibitor, a FAS (fatty acid synthase) inhibitor, a PDE (phosphodiesterase) inhibitor, a thyroid hormone B agonist, an UCP-1 (uncoupling protein 1), 2, or 3 activator, an acyl-estrogen, a glucocorticoid antagonist, an 11 HSD-1 (11-beta hydroxy steroid dehydrogenase type 1) inhibitor, a SCD-1 (stearoyl-CoA desaturase-1) inhibitor, a dipeptidyl peptidase IV (DP-IV) inhibitor, a lipase inhibitor, a fatty acid transporter inhibitor, a dicarboxylate transporter inhibitor, a glucose transporter inhibitor, a phosphate transporter inhibitor, and pharmaceutically acceptable salts and esters thereof.

Suitable appetite-regulating agents (appetite suppressants) comprise sibutramine or the mono- and bisdemethylated active metabolites of sibutramine; fenfluramine or dexfenfluramine; mazindol, diethylpropion or phentermine; leptin or modified leptin; dexamphetamine and amphetamine.

Suitable lipase inhibitors comprise orlistat, panclicins, lipase inhibitors isolated from micro organisms such as lipstatin (from *Streptomyces toxytricirn*), ebelactone B (from *Streptomyces aburaviensis*), synthetic derivatives of these compounds; 2-oxy-4H-3,1-benzoxazin4-one derivatives like Alizyme's ATL-962 or structurally related compounds;

2-amino4H-3,1-benzoxazin4-one derivatives or extracts of plants known to possess lipase inhibitory activity, e.g. extracts of *Alpinia officinarum* or compounds isolated from such extracts like 3-methylethergalangin (from *A. officinarum*);

Suitable CB$_1$-cannabinoid antagonists include rimonabant, SLV319, SR147778 and CP-945598.

Suitable cardiovascular active agents comprise angiotensin 11 receptor antagonists, e.g. abitesartan, benzyllosartan, candesartan, elisartan, embusartan, enoltasosartan, eprosartan, fonsartan, forasartan, glycyllosartan, irbesartan, isoteoline, losartan, milfasartan, olmesartan, opomisartan, pratosartan, ripisartan, saprisartan, saralasin, sarmesin, tasosartan, telmisartan, valsartan, zolasartan; Kissei KRH-94, Lusofarmaco LR-B/057, Lusofarmaco LR-B/081, Lusofarmaco LR B/087, Searle SC-52458, Sankyo CS-866, Takeda TAK-536, Uriach UR-7247, A-81282, A-81988, BIBR-363, BIBS39, BIBS-222, BMS-180560, BMS-184698, CGP-38560A, CGP-48369, CGP-49870, CGP-63170, CI-996, CV-11194, DA-2079, DE-3489, DMP-811, DuP-167, DuP-532, GA-0056, E-4177, EMD-66397, EMD-73495, EXP-063, EXP-929, EXP-3174, EXP-6155, EXP-6803, EXP-7711, EXP-9270, FK-739, HN-65021, HR-720, ICI-D6888, ICI-D7155, ICI-D8731, KRI-1177, KT3-671, KW-3433, L-158809, L-158978, L-159282, L-159689, L-159874, L-161177, L-162154, L-162234, L-162441, L-163007, L-163017, LY-235656, LY-285434, LY-301875, LY-302289, LY-315995, ME-3221, PD-123177, PD-123319, PD-150304, RG-13647, RWJ-38970, RWJ-46458, S-8307, S-8308, SL-91.0102, U-96849, U-97018, UP-269-6, UP-275-22, WAY-126227, WK-1492.2K, WK-1360, X-6803, XH-148, XR-510, YM-358, YM-31472, ZD-6888, ZD-7155 and ZD-8731 or any physiologically compatible salts, solvates, prodrugs or esters thereof; daglutril; non-selective alpha-adrenoceptor antagonists, e.g. tolazoline or phenoxybenzamine; selective alpha-adrenoceptor antagonists, e.g. doxazosin, prazosin, terazosin or urapidil; beta-adrenoceptor antagonists, e.g. acebutolol, alprenolol, atenolol, betaxolol, bisoprolol, bupranolol, carazolol, carteolol, celiprolol, mepindolol, metipranolol, metoprolol, nadolol, oxprenolol, penbutolol, pindolol, propranolol, sotalol and timolol; mixed antagonists of alpha- and beta-adrenoceptors, e.g. carvedilol or labetolol; ganglion blockers, e.g. reserpine or guanethidine; alpha2-adrenoceptor agonists (including centrally acting alpha2-adrenoceptor agonists), e.g. clonidine, guanfacine, guanabenz methyldopa and moxonidine; renin-inhbitors, e.g. alskiren; ACE-inhbitors, e.g. benazepril, captopril, cilazapril, enalapril, fosinopril, imidapril, lisinopril, moexipril, quinapril, perindopril, ramipril, spirapril or trandolapril; mixed or selective endothelin receptor antagonists e.g. atrasentan, bosentan, clazosentan, darusentan, sitaxsentan, tezosentan, BMS-193884 or J-104132; direct vasodilators, e.g. diazoxide, dihydralazine, hydralazine or minoxidil; mixed ACE/NEP-inhbitors, e.g. omapatrilat; ECE-inhbitors, e.g. FR-901533; PD-069185; CGS-26303; CGS-34043; CGS-35066; CGS-30084; CGS-35066; SM-19712; Ro0677447; selective NEP-inhibitors; vasopressin antagonists, aldosterone receptor antagonists, e.g. eplerenone or spironolactone; angiotensin vaccine; and urotensin II receptor antagonists.

Suitable diuretics comprise thiazide diuretics, e.g. althiazide, bemetizide, bendroflumethiazide, benzylhydrochlorothiazide, benzthiazide, buthiazide, chlorothiazide, cyclothiazide, hydrochlorothiazide, hydroflumethiazide, methyclothiazide, paraflutizide, polythiazide, teclothiazide, trichlormethiazide; thiazide analogue diuretics, e.g. chloraminofenamide, chlortalidone, clofenamide, clopamide, clorexolone, fenquizone, indapamide, mefruside, metolazone, quinethazone, tripamide, xipamide; loop diuretics, e.g. azosemide, bumetanide, furosemide, piretanide, torsemide; potassium sparing diuretics, e.g. amiloride, potassium canrenoate, spironolactone, triamterene or any physiologically compatible tautomers, salts, solvates, prodrugs or esters of any afore mentioned diuretic.

Suitable active agents which alter lipid levels comprise compounds which alter lipid metabolism, such as antihyperlipidemic active ingredients and antilipidemic active ingredients like HMGCoA reductase inhibitors, e.g. atorvastatin, berivastatin, cerivastatin, crilvastatin, fluvastatin, glenvastatin, lovastatin, mevastatin, pitavastatin, pravastatin, rosuvastatin, simvastatin or any physiologically compatible salts, solvates, prodrugs or esters thereof; inhibitors of cholesterol transport/of cholesterol uptake; inhibitors of bile acid reabsorption or inhibitors of the microsomal triglyceride transfer protein (MTP); compounds which reduce food intake, PPAR (=peroxisome proliferator-activated receptors) and RXR agonists and active agents which act on the ATP-dependent potassium channel of the beta cells; fibric acids, e.g. bezafibrate, ciprofibrate, clofibrate, fenofibrate or gemfibrozil; cholestyramine, colestipol, probucol, ezetimibe and dextrothyroxine; HMGCoA synthase inhibitor, a cholesterol absorption inhibitor, an acyl coenzyme A-cholesterol acyl transferase (ACAT) inhibitor, a cholesteryl ester transfer protein (CETP) inhibitor, a squalene synthetase inhibitor, an anti-oxidant, a PPAR α agonist, a FXR receptor modulator, a LXR receptor agonist, a lipoprotein synthesis inhibitor, a renin angiotensin system inhibitor, a microsomal triglyceride transport inhibitor, a bile acid reabsorption inhibitor, a PEAR8 agonist, a triglyceride synthesis inhibitor, a transcription modulator, a squalene epoxidase inhibitor, a low density lipoprotein receptor inducer, a platelet aggregation inhibitor, a 5-LO or FLAP inhibitor, a PPAR 8 partial agonist, and niacin or a niacin receptor agonist, and pharmaceutically acceptable salts and esters thereof.

Further active agents which may be suitable for use in combination with the compound of Formula I according to the present invention may be selected from the group consisting of CART agonists, H3 antagonists, TNF agonists, CRF agonists, CRF BP antagonists, urocortin agonists, beta3-agonists, MSH (melanocyte-stimulating hormone) agonists, serotonin-reuptake inhibitors, mixed serotonin- and noradrenaline-reuptake inhibitors, 5HT modulators, MAO inhibitors, galanin antagonists, growth hormone, growth hormone-releasing compounds, TRH agonists, modulators of uncoupling proteins 2 or 3, leptin agonists, dopamine agonists (bromocriptine, doprexin), RXR modulators, hCNTF agonists and TR-beta-agonists.

Preferred pharmaceutical combination compositions according to the invention comprise combinations of at least one compound of Formula I and at least one biguanide; at least one compound of Formula I and at least one fibric acid; at least one compound of Formula I and at least one HMG-COA reductase inhibitor; and at least one compound of Formula I and at least one insulin sensitizer.

Preferred compounds of Formula I for combination with one or more of the above mentioned active agents are 4-phenyl-piperazine-1-sulfonic acid amide; 4-(2-chloro-phenyl)-piperazine-1-sulfonic acid amide; 4-(2-methoxy-phenyl)-piperazine-1-sulfonic acid amide; 4-pyridin-4-yl-piperazine-1-sulfonic acid amide; 4-pyrimidin-2-yl-piperazine-1-sulfonic acid amide; 4-(4-fluoro-phenyl)-piperazine-1-sulfonic acid amide; 4-(4-chloro-3-trifluoromethyl-phenyl)-piperazine-1-sulfonic acid amide and/or 4-(3-chloro-5-trifluoromethyl-pyridin-2-yl)-piperazine-1-sulfonic acid amide.

Metformine is the preferred biguanide for combination with at least one compound of general Formula I.

Preferred fibric acids for combination with at least one compound of general Formula I are bezafibrate, ciprofibrate, clofibrate, fenofibrate and/or gemfibrozil. Fenofibrate is most preferred.

Preferred HMGCoA reductase inhibitors for combination with at least one compound of general Formula I are atorvastatin, berivastatin, cerivastatin, crilvastatin, fluvastatin, glenvastatin, lovastatin, mevastatin, pitavastatin, pravastatin, rosuvastatin and/or simvastatin or any physiologically compatible salts, solvates, prodrugs or esters thereof. Most preferred are simvastatin, lovastatin and/or pravastatin.

Preferred insulin sensitizers for combination with at least one compound of general Formula I are thiazolidinediones, in particular troglitazone, ciglitazone, pioglitazone and/or rosiglitazone. Rosiglitazone and pioglitazone are most preferred.

More preferred combinations according to the invention are the combinations of 4-phenyl-piperazine-1-sulfonic acid amide with metformine; 4-phenyl-piperazine-1-sulfonic acid amide with fenofibrate; 4-phenyl-piperazine-1-sulfonic acid amide with simvastatin and 4-phenyl-piperazine-1-sulfonic acid amide with rosiglitazone.

In one embodiment of the pharmaceutical combination compositions in accordance with the invention as described above, the compounds of Formula I can be obtained and administered together with the different active agents, e.g. in a combined unit dosage form such as a single tablet or capsule, i.e. in a physical combination. In such a combined unit dosage form, the compound of Formula I and the different active agents can be segregated from each other, e.g. by arrangement in different layers of the tablet and the use of inert intermediate layers known in the art; or by disposal in different compartments in the capsule. The corresponding active agents or their pharmaceutically acceptable salts may also be used in form of their hydrates or include other solvents used for crystallization. A unit dosage form may be a fixed combination. A unit dosage form, in particular a fixed combination of the compound of general Formula I and one or more of the different active agents is a preferred alternative of this embodiment.

In another embodiment the compounds of Formula I and the different active agents can be obtained and administered in two or more separate unit dosage forms, e.g. in two or more tablets or capsules, the tablets or capsules being physically segregated from each other. The two or more separate unit dosage forms can be administered simultaneously or separately, e.g. sequentially one after the other in either order. Thus, the compounds of Formula I and the different active agents can be administered in either order at the same time or at different times spread over the day, the optimal dosage regimen usually being determined by prescription of a physician.

The following examples are intended to illustrate the invention in further detail without limiting its scope.

EXAMPLE 1

Reaction of 5-bromo-2-hydroxy acetophenone with N-Boc-4-piperidone

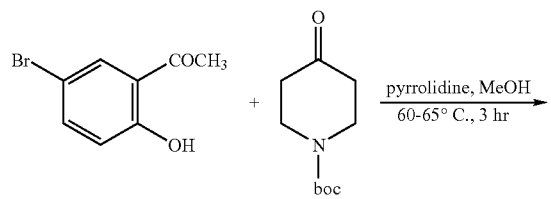

-continued

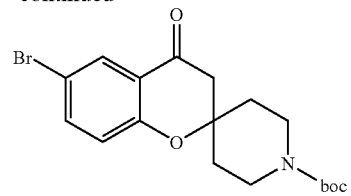

In a 500 ml 3-necked flask, fitted with a reflux condenser, a $CaCl_2$ gaurd tube and a magnetic needle, 0.1 mole of N-Boc-4-piperidone (19.5 g) and 0.116 mole of pyrrolidine (8.95 g), dissolved in 100 ml of anhydrous MeOH at ambient temperature were added to 0.0837 mole 5-bromo-2-hydroxyacetophenone (18 g). The reaction mixture was stirred under reflux at 60-65° C. for about 3 hours. The reaction mixture was transferred to a rotary flask, and MeOH was distilled off to obtain an orange viscous liquid. 75 ml of water was added, and the product was extracted four times with 100 ml portions of ethyl acetate. The aqueous layer was discarded, and the organic layer was dried over anhydrous $Na_2SO_4$. Ethyl acetate was distilled off, and an orange viscous oil was obtained that was thoroughly dried in vacuo. Further purification by column chromatography with ethyl acetate/petrolether 10/90 yielded 28,7 g (87%) of a pale yellow crystalline solid. Melting Point: 140-143° C.

TABLE 3

Further compounds (X—Y is $H_2C$—C=O) prepared in excellent yields by following the same general procedure as in example 1.

| R3 | R4 | R5 | R6 | m.p./° C. |
|----|----|----|----|-----------|
| H | H | H | H | 89-92 |
| H | Br | H | H | 140-143 |
| H | OCH3 | H | H | 146-149 |
| H | F | H | H | 118-122 |
| H | H | F | H | 104-107 |
| H | NH2 | H | H | 183-185 |
| H | CN | H | H | 178-181 |
| H | H | NH—COCF3 | H | 194-196 |
| H | NH—COCF3 | H | H | 230-232 |
| H | Cl | H | Br | 126-128 |
| H | H | Br | H | 112-115 |

EXAMPLE 2

Protection Group Bond Cleavage

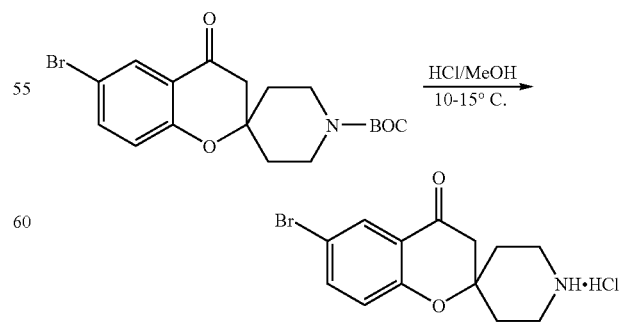

In a 1 liter 3-necked flask, fitted with a bubbler, a magnetic needle and a set up to pass HCl gas, 26.0 g of 5-bromo-N- bocspirocyclic ether derivative was dissolved in 300 ml methanol. HCl gas was passed through the solution until a white solid started precipitating out. This indicated completion of the reaction and saturation of HCl in the reaction mixture. The reaction mixture was transferred to a rotary flask and methanol was removed under vacuum. A pale yellow solid was obtained, which was washed well with petroleum ether, filtered through a Bucker's funnel and thoroughly dried in vacuo. 22 g HCl salt was obtained as an off white crystalline solid. Melting Point: 273-274° C.

TABLE 4

Further compounds (X—Y is H$_2$C—C=O) prepared in excellent yields by following the same general procedure as in example 2.

| R3 | R4 | R5 | R6 | M.P./° C. |
|----|----|----|----|-----------|
| H | H | H | H | 206-207 |
| H | Br | H | H | 273-274 |
| H | OCH3 | H | H | 199-202 |
| H | F | H | H | 223-225 |
| H | H | F | H | 200-206 |
| H | NH2 | H | H | 211-220 |
| H | CN | H | H | 131-135 |
| H | Cl | H | Br | 133-134 |
| H | H | Br | H | 222-228 |

EXAMPLE 3

Preparation of 5-Bromo-spirocyclic ether sulfamide Derivative

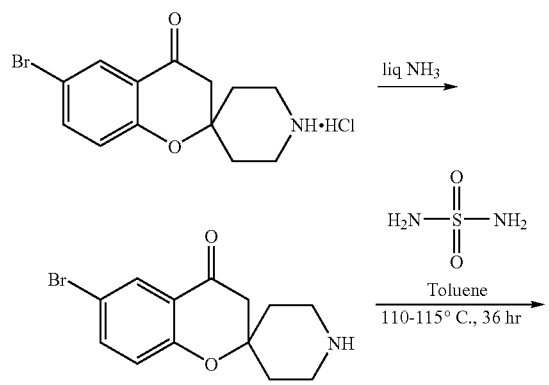

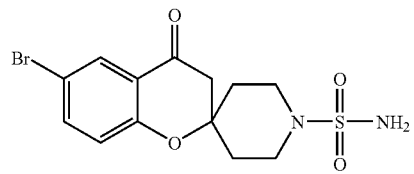

16 g of the 5-bromo HCl salt from Example 2 were added to 250 ml of water and neutralized by adding aqueous NH$_3$ until pH=~10. A yellow sticky paste was formed which was extracted four times with 100 ml portions of ethyl acetate. The organic layer was then dried over anhydrous sodium sulfate and finally concentrated using a rotary evaporator to obtain the free base as dark yellowish orange viscous oil. The free base was thoroughly dried under vacuum to remove any traces of ethyl acetate. The free base was then dissolved in toluene and solid sulfamide was added. The reaction mixture was stirred under reflux at 110-115° C. for about 14 hrs. TLC was checked at regular intervals. There were still spots of starting material. Thus 0.2 equivalent of sulfamide was again added and the reaction mixture was stirred under reflux overnight.

A sticky solid which formed during the reaction was removed by dissolving in DCM-MeOH mixture. The toluene solvent was decanted into a rotary flask. Some of the solid which did not dissolve in DCM-MeOH or any other solvent was dissolved in DMF (~10-15 ml). Half of the solvent was distilled off using a rotary evaporator. The entire quantity was not distilled off as the product was difficultly soluble in any solvent. Hence, in the remaining quantity of solvent, silica (mesh 230-400) was added and a slurry was made as such for column chromatography, starting first with DCM and then changing to DCM:MeOH 95:5. The resulting pale yellow solid was crystallized using DCM:MeOH:Petrolether. The yield was 8.2 g of a white crystalline solid with a melting of 202-205° C.

The diamino equivalents (R1, R2=hydrogen) of compounds 1 to 6 and 8 to 78 can be prepared in excellent yields by following the same general procedure described in examples 1 to 3 above.

TABLE 5

Further compounds of general Formula I (X is CH$_2$ and Y is C=O).

| Ex. No. | R1 | R2 | R3 | R4 | R5 | R6 | m.p./° C. |
|---------|----|----|----|----|----|----|-----------|
| 1 | H | H | H | H | H | H | 172-174 |
| 2 | H | H | H | Br | H | H | 205-208 |
| 3 | H | H | H | OCH$_3$ | H | H | 172-177 |
| 4 | H | H | H | Cl | H | H | |
| 5 | H | H | H | F | H | H | 177-186 |
| 6 | H | H | H | H | F | H | 163-166 |
| 7 | H | H | H | CH$_3$ | CH$_3$ | H | |
| 8 | H | H | H | CH$_3$ | H | H | |

TABLE 5-continued

Further compounds of general Formula I (X is CH$_2$ and Y is C=O).

| Ex. No. | R1 | R2 | R3 | R4 | R5 | R6 | m.p./° C. |
|---|---|---|---|---|---|---|---|
| 9 | H | H | H | H | phenyl ring (R5–R6) | | |
| 10 | H | H | H | H | OCH$_3$ | H | |
| 11 | H | H | OCH$_3$ | H | H | H | |
| 12 | H | H | H | H | OCH$_2$C$_6$H$_5$ | CH$_3$ | |
| 13 | H | H | phenyl ring (R3–R4) | | H | H | |
| 14 | H | H | H | Cl | H | Cl | |
| 15 | H | H | H | H | OCH$_3$ | OCH$_3$ | |
| 16 | H | H | H | OCH$_3$ | OCH$_3$ | H | |
| 17 | H | H | OCH$_3$ | OCH$_3$ | OCH$_3$ | H | |
| 18 | H | H | OCH$_3$ | H | OCH$_3$ | H | |
| 19 | H | H | OCH$_3$ | H | OCH$_3$ | CH$_3$ | |
| 20 | H | H | H | H | COCH$_3$ | H | |
| 21 | H | H | H | F | H | F | |
| 22 | H | H | OCH$_3$ | furan ring (R4–R5) | | OCH$_3$ | |
| 23 | H | H | H | C$_2$H$_5$ | H | H | |
| 24 | H | H | H | H | OCOCH$_3$ | H | |
| 25 | H | H | H | H | dioxane ring (R5–R6) | | |
| 26 | H | H | H | NH$_2$ | H | H | |
| 27 | H | H | H | H | HNC$_2$H$_5$ | C$_3$H$_7$ | |
| 28 | H | H | H | C≡N | H | H | |
| 29 | H | H | H | H | HNCOCF$_3$ | C$_3$H$_7$ | |
| 30 | H | H | H | tert.C$_4$H$_9$ | H | tert. C$_4$H$_9$ | |
| 31 | H | H | OCH$_3$ | H | H | OCH$_3$ | |
| 32 | H | H | H | HNCOCF$_3$ | H | H | |
| 33 | H | H | H | H | H | Cl | |
| 34 | H | H | H | H | CH$_3$ | H | |
| 35 | H | H | H | H | HNCOCH$_3$ | CH$_2$CH=CH$_2$ | |
| 36 | H | H | H | H | OCH$_2$COCH$_3$ | H | |
| 37 | H | H | OC$_2$H$_4$OC$_2$H$_5$ | H | H | H | |
| 38 | H | H | OCH$_2$C$_6$H$_5$ | H | H | H | |
| 39 | H | H | OCH$_2$CH$_2$CH(CH$_3$)$_2$ | H | H | H | |
| 40 | H | H | H | OC$_2$H$_5$ | H | H | |
| 41 | H | H | H | H | OCH$_3$ | OCH$_2$C$_6$H$_5$ | |
| 42 | H | H | H | CH=CHCH$_3$ | HNCOCH$_3$ | C$_3$H$_7$ | |
| 43 | H | H | H | F | H | H | |
| 44 | H | H | H | CH$_3$ | cyclopentane ring (R5–R6) | | |
| 45 | H | H | H | Cl | CH$_3$ | H | |
| 46 | H | H | H | Br | H | Br | |
| 47 | H | H | H | CH$_3$ | H | NO$_2$ | |
| 48 | H | H | H | C≡N | Cl | Br | |
| 49 | H | H | Cl | H | H | H | |
| 50 | H | H | H | H | NO$_2$ | H | |
| 51 | H | H | H | H | Cl | H | |

TABLE 5-continued

Further compounds of general Formula I (X is CH₂ and Y is C=O).

| Ex. No. | R1 | R2 | R3 | R4 | R5 | R6 | m.p./° C. |
|---|---|---|---|---|---|---|---|
| 52 | H | H | 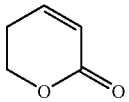 | | H | H | |
| 53 | H | H | H | F | H | Cl | |
| 54 | H | H | H | OCH₃ | CH₃ | H | |
| 55 | H | H | H | Cl | H | Br | 192-195 |
| 56 | H | H | H | iC₃H₇ | H | H | |
| 57 | H | H | F | H | H | H | |
| 58 | H | H | H | OCF₃ | H | H | |
| 59 | H | H | H | CH₃ | H | CH₃ | |
| 60 | H | H | H | Br | H | Cl | |
| 61 | H | H | OCH₃ | H | OCH₃ | I | |
| 62 | H | H | H | CH₃ | H | HNCO O-tert.-C₄H₉ | |
| 63 | H | H | H | F | H | 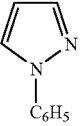 | |
| 64 | H | H | H | F | H |  | |
| 65 | H | H | H | Cl | OCH₃ | H | |
| 66 | H | H | H | NSO₂CH₃ | H | H | |
| 67 | H | H | H | Br | H | H | 186-188 |
| 68 | H | H | OCH₃ | H | OCH₃ | Cl | |
| 69 | H | H | H | H | OCH₂-3-C₆H₄CF₃ | H | |
| 70 | H | H | OCH₂CH₃ | H | H | H | |
| 71 | H | H | H | OCH₂CH₃ | H | H | |
| 72 | H | H | H | 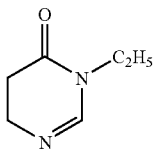 | | H | |
| 73 | H | H | H | Cl |  | | |
| 74 | H | H | H | OCH₃ |  | | |
| 75 | H | H | H | H |  | | |
| 76 | H | H | H |  | | H | |
| 77 | H | H | H | COOCH₃ | H | H | |

EXAMPLE 4

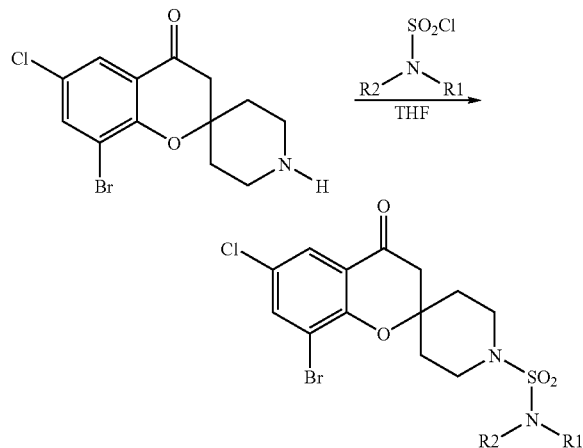

One equivalent of benzopyran derivative in THF and 1 equivalent of sulfamoylchloride derivative in THF were reacted overnight at room temperature in the presence of 1.1 equivalent of triethylamine. The reaction mixture was evaporated and purified by liquid/liquid extraction with 10% tartatic acid and ethyl acetate. The organic layers were dried on sodium carbonate and evaporated. The LC-MS data are summarized below.

TABLE 6

Further compounds of Formula I (X is $CH_2$ and Y is C=O) prepared in excellent yields by following the same procedure as in example 4.

| Example No | Structure | Molecular Weight | ELSD Retention time/min |
|---|---|---|---|
| 78 | 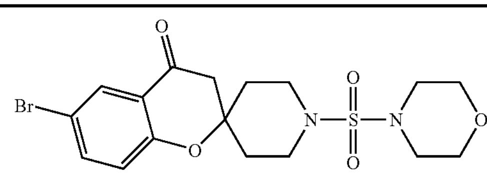 | 445.3319 | 5.62 |
| 79 | 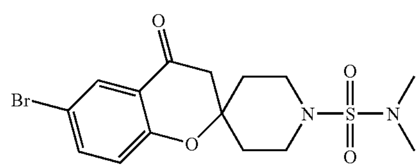 | 403.2951 | 5.72 |
| 80 | 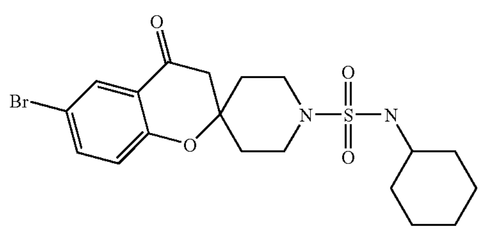 | 457.3865 | 5.85 |
| 81 | 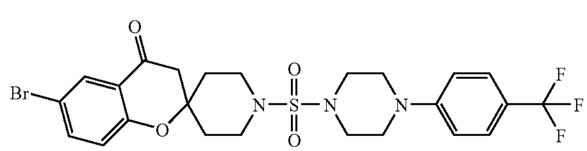 | 588.4425 | 6.78 |
| 82 | 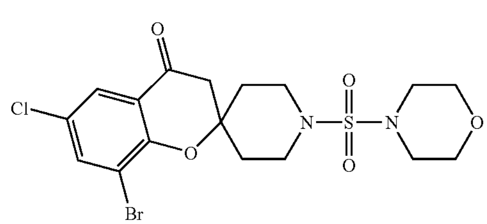 | 479.777 | 5.87 |

TABLE 6-continued

Further compounds of Formula I (X is CH$_2$ and Y is C=O) prepared in excellent yields by following the same procedure as in example 4.

| Example No | Structure | Molecular Weight | ELSD Retention time/min |
|---|---|---|---|
| 83 | 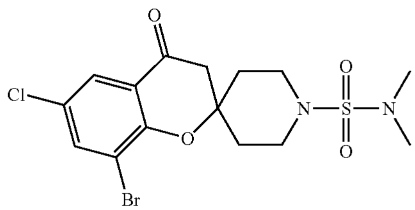 | 437.7402 | 6.01 |
| 84 | 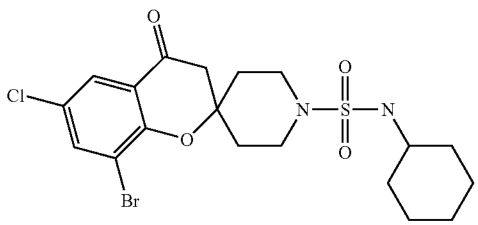 | 491.8316 | 6.51 |
| 85 | 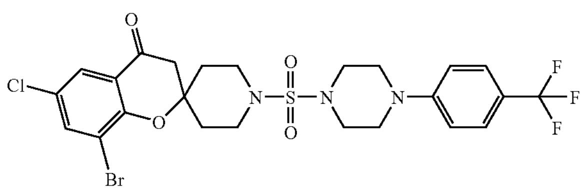 | 622.8876 | 6.95 |
| 86 | 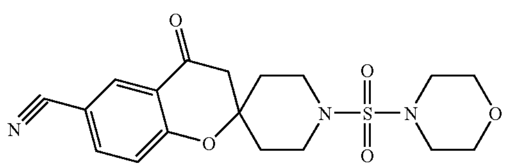 | 391.4459 | 5 |
| 87 | 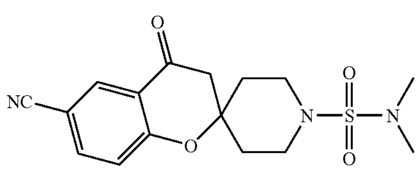 | 349.4091 | 5.1 |
| 88 | 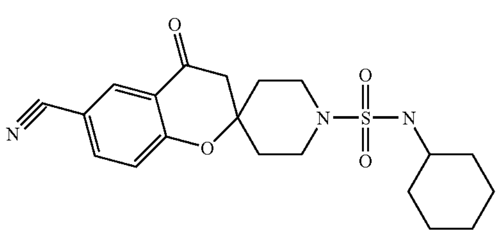 | 403.5005 | 5.68 |
| 89 | 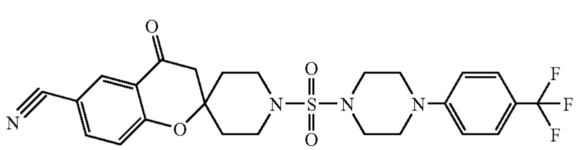 | 534.5565 | 6.33 |

TABLE 6-continued

Further compounds of Formula I (X is CH$_2$ and Y is C=O) prepared in excellent yields by following the same procedure as in example 4.

| Example No | Structure | Molecular Weight | ELSD Retention time/ min |
|---|---|---|---|
| 90 | 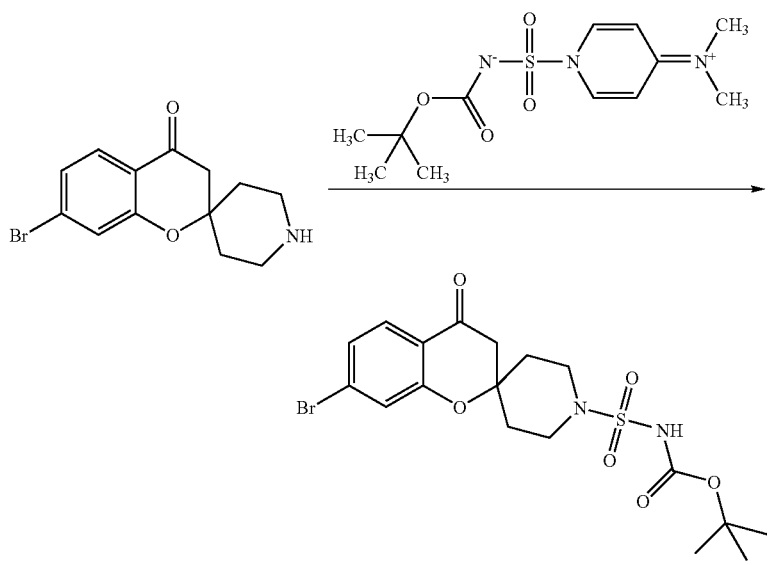 | 381.4507 | 4.35 |

EXAMPLE 5

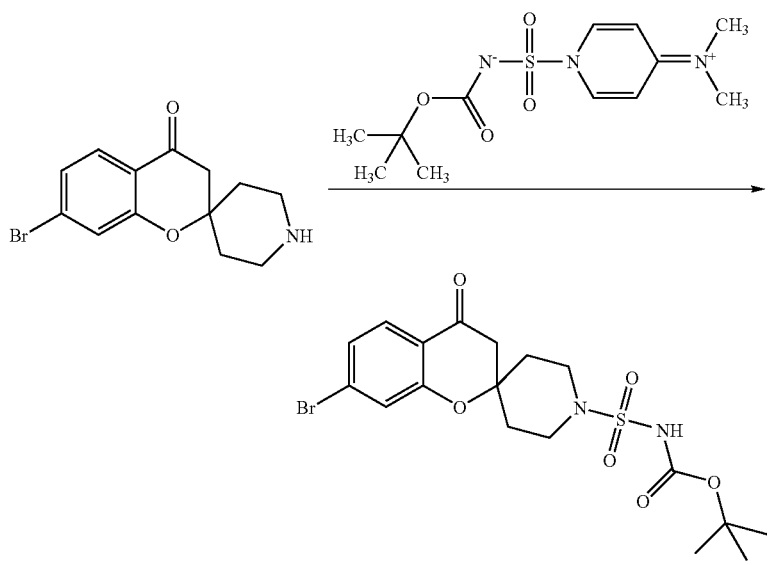

A mixture of 1.2 g benzopyran, 0.6 ml of triethyl amine and 1.2 g DMAP reagent III in 10 ml dichloromethane was stirred at room temperature for 4 hours. 37% hydrochloric acid was added dropwise, and the resulting mixture was stirred for 30 minutes. The organic layer was washed with water several times, dried over Na$_2$SO$_4$ and evaporated. Yield: 0.89 g. LC-MS: ELSD at 5.96 min. Protection group bond cleavage was performed as in Example 2.

EXAMPLE 6

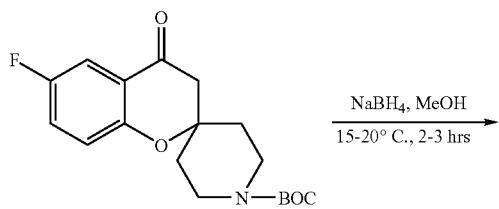

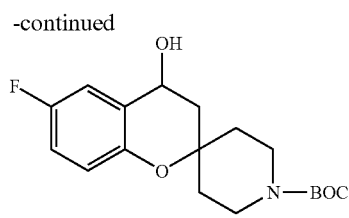

In a three necked 500 ml flask equipped with stirring bar and bubbler, 29 g of the pyranone derivative were dissolved in 250 ml methanol. The reaction mixture was cooled to 10° C., and sodium borohydride (6.6 g) was added portion wise over 0.5 hour. One hour later the solvent was removed under vacuum. The solid was taken up in 400 ml water, and the product was extracted with ethyl acetate. The organic layer was finally washed with 250 ml of brine solution and dried over anhydrous sodium sulfate. The solvent was concentrated to obtain 30 g of a pale yellow oily product. The sulfamyl-/ sulfamide group substitution was performed as in Example 3 or 4.

EXAMPLE 7

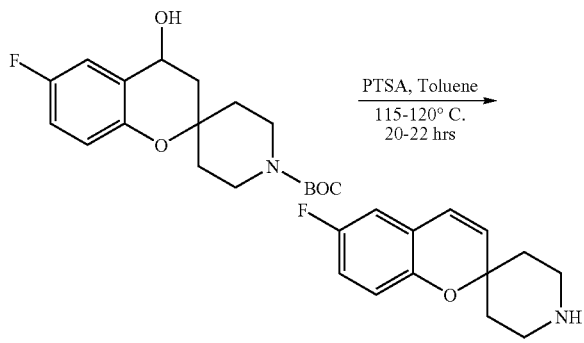

Using a 500 ml three necked flask equipped with a water condenser, stirring bar and guard tube, the above synthesized hydroxyl compound (21.0 gm) was dissolved in 350 ml of toluene and refluxed for 10 hours together with PTSA (12.9 gm). Toluene was completely removed under vacuum, and 400 ml of dichloromethane was added to the residue and stirred to obtain a clear solution. The dichloromethane solution was washed twice with 100 ml portions of 0% NaHCO$_3$ and then with 200 ml of saturated salt solution. The organic layer was dried over anhydrous sodium sulfate. The dichloromethane layer was concentrated to obtain 31 g of crude product. Finally the crude product was purified using flash column chromatography over silica gel (230-400 mesh) using dichloromethane (94%): methanol (5%): ammonia (1%) as the elution system. Yield: 13 g of a colorless solid.

TABLE 7

Further compounds of Formula I prepared in excellent yields by following the same general procedure as in Example 7.

| R3 | R4 | R5 | R6 | m.p./° C. |
|----|------|----|----|-----------|
| H  | OCH3 | H  | H  | 238-240   |
| H  | Br   | H  | H  | 258-260   |
| H  | F    | H  | H  | 218-220   |

The sulfamyl-/sulfamide group introduction was performed as in Example 3 or 4.

EXAMPLE 8

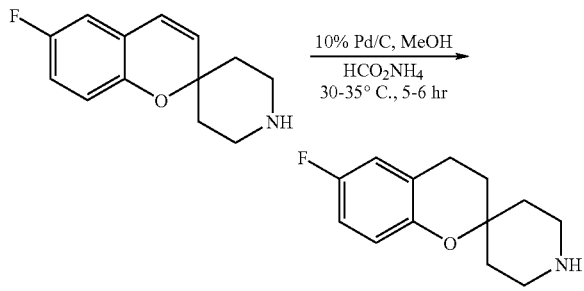

5.0 g of 10% Pd/C was stirred under N$_2$ atmosphere in a 1 litre three necked flask equipped with N$_2$-adaptor and bubbler. Under cooling methanol (200 ml) was added and subsequently the fluoro derivative (17 g) of Example 7 dissolved in methanol (150 ml) was charged directly in the reaction flask. After 15 min of stirring, ammonium formate (17.4 gm) was charged portion wise at ambient temperature. After complete addition, reaction was warmed to 30-35° C. and maintained for 5-6 hrs. The catalyst was filtered over highflow bed and the filtrate was concentrated to get 21 g of the solid product. To this solid, 20% K$_2$CO$_3$ solution (100 ml) was added and product was extracted by ethyl acetate (3×100 ml). All organic layers were combined and washed with saturated solution (200 ml) and dried over anhydrous sodium sulfate. The solvent was evaporated completely to get the product, which was converted to its HCl salt (colourless solid, 14,5 g, mp. 218-220° C.).

The sulfamyl-/sulfamide group introduction was preformed as any of Examples 3 and/or 4.

EXAMPLE 9

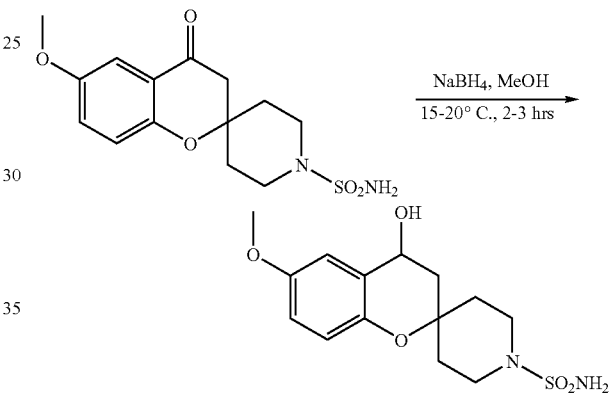

50 mg of the sulfamide were dissolved in 5 ml methanol. The reaction mixture was cooled to 10° C. and sodium borohydride was added portion wise in 0.5 hr. One hour later the solvent was removed under vacuum. Water was added to the solid residue and the product was extracted with ethyl acetate. The organic layer was finally washed with brine solution and dried over anhydrous sodium sulfate. The solvent was concentrated to get 43,5 mg of a oily product.

EXAMPLE 10

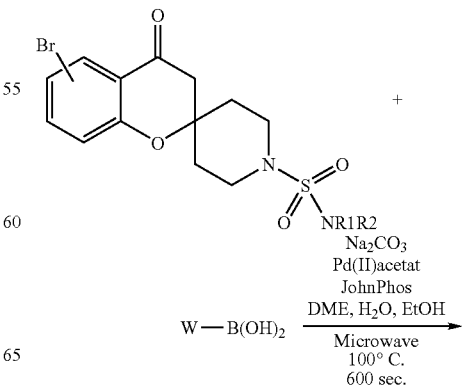

-continued

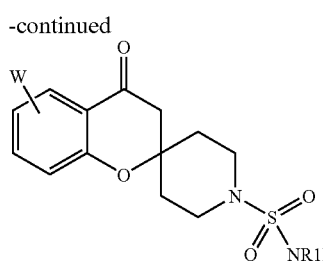

Pd-acetate (0.01 mmol), 0.01 mmol of 2-(di-tert-butylphosphino)biphenyl ["JohnPhos"] and 0.3 mmol of $Na_2CO_3$ are stirred together with 2 ml of the solvent mixture (DME/$H_2O$/EtOH: 7/3/2) for 5 minutes. Subsequently 0.9 mmol of the bromo-substituted sulfamide and 0.1 mmol of the boronic acid in 3 ml of the same solvent mixture are added. The microwave vial is capped and heated for 600 sec at 100° C. After the reaction, the mixture was filtered over Celite, concentrated and analyzed by LC-MS.

TABLE 8

Further compounds of Formula I (X is $CH_2$ and Y is C═O) prepared in excellent yields by following the same procedure as in example 10.

| Example No | Structure | ELSD Retention time/min |
|---|---|---|
| 91 | 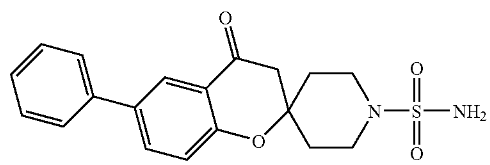 | 5.40 |
| 92 | 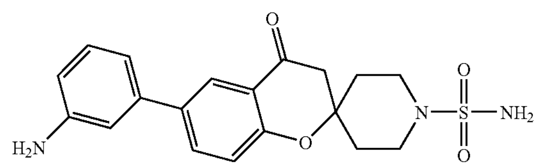 | 4.60 |
| 93 | 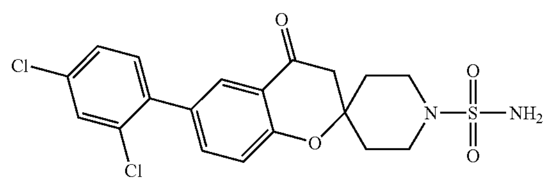 | 6.10 |
| 94 | 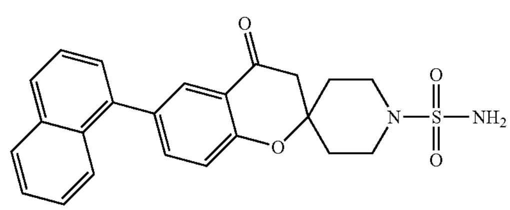 | 5.94 |
| 95 | 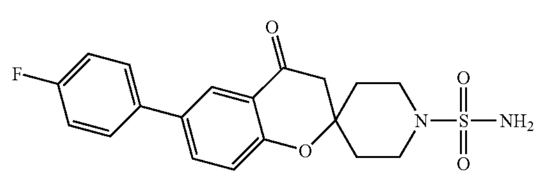 | 5.44 |
| 96 | 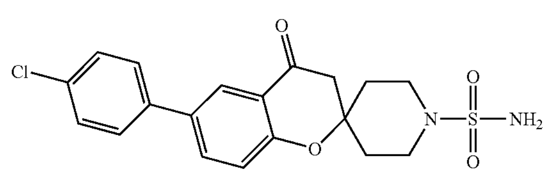 | 5.81 |

TABLE 8-continued

Further compounds of Formula I (X is CH$_2$ and Y is C=O) prepared in
excellent yields by following the same procedure as in example 10.

| Example No | Structure | ELSD Retention time/min |
|---|---|---|
| 97 | 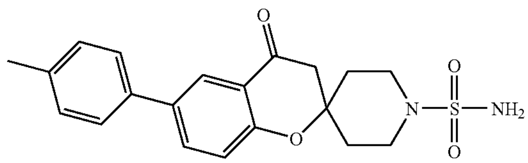 | 5.71 |
| 98 | 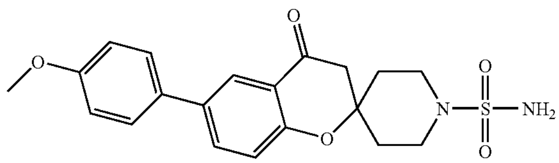 | 5.31 |
| 99 | 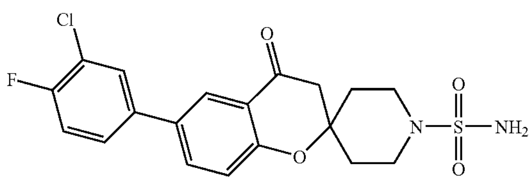 | 5.82 |
| 100 | 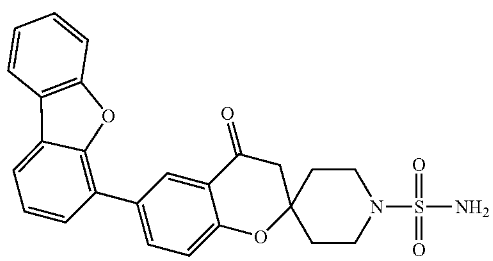 | 6.22 |
| 101 | 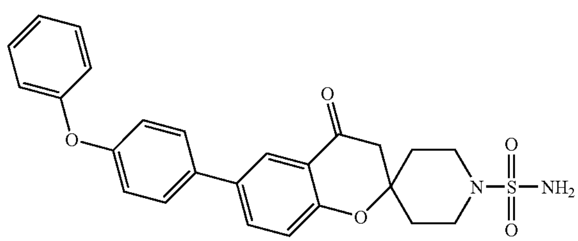 | 6.20 |
| 102 | 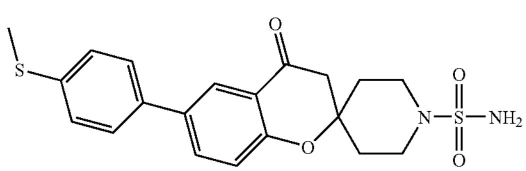 | 5.72 |
| 103 | 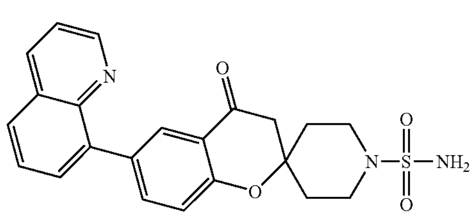 | 5.19 |

TABLE 8-continued

Further compounds of Formula I (X is CH$_2$ and Y is C═O) prepared in excellent yields by following the same procedure as in example 10.

| Example No | Structure | ELSD Retention time/min |
|---|---|---|
| 104 | 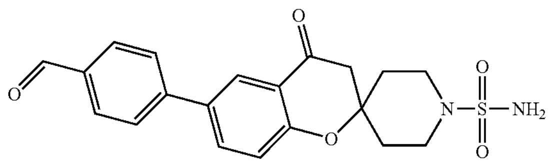 | 4.94 |
| 105 | 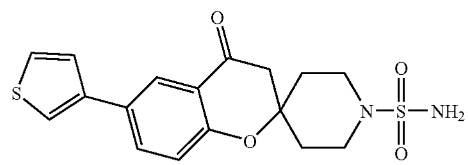 | 5.23 |
| 106 | 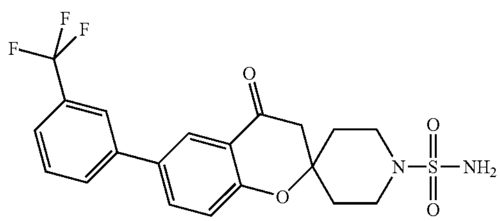 | 5.86 |
| 107 | 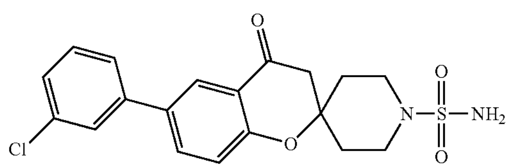 | 5.77 |
| 108 | 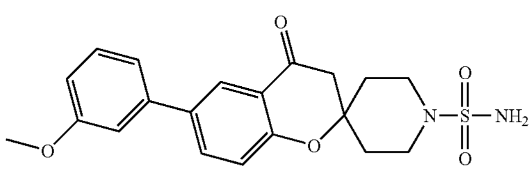 | 5.36 |
| 109 | 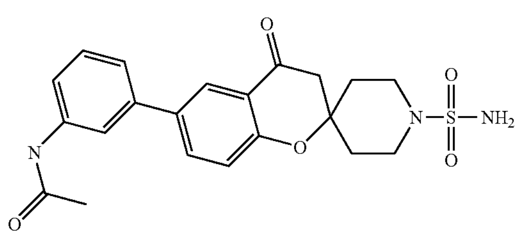 | 4.42 |
| 110 | 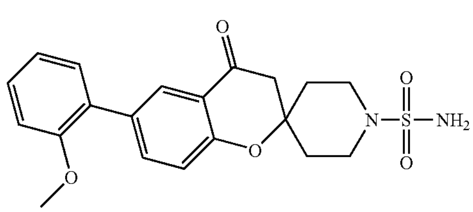 | 5.36 |

TABLE 8-continued

Further compounds of Formula I (X is CH$_2$ and Y is C=O) prepared in
excellent yields by following the same procedure as in example 10.

| Example No | Structure | ELSD Retention time/min |
|---|---|---|
| 111 | 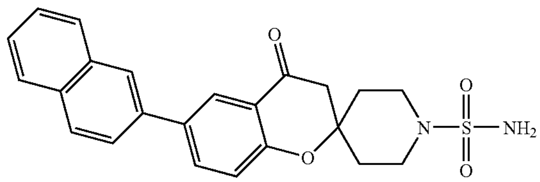 | 5.97 |
| 112 | 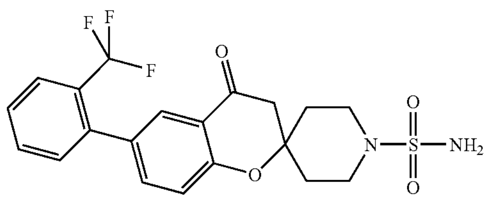 | 5.66 |
| 113 | 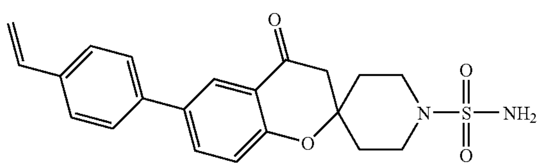 | 5.80 |
| 114 | 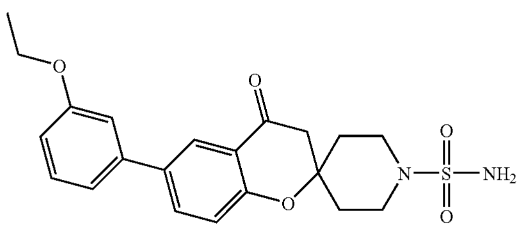 | 5.67 |
| 115 | 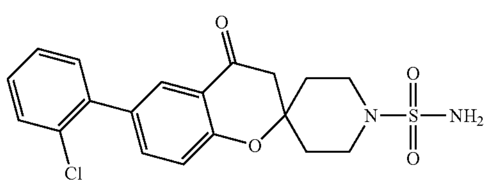 | 5.57 |
| 116 | 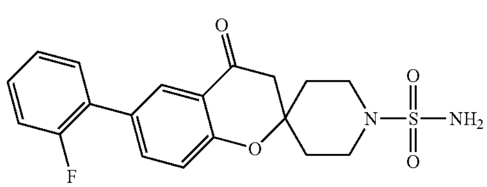 | 5.39 |
| 117 | 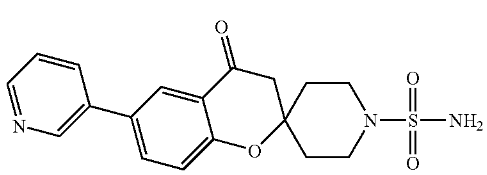 | 4.17 |

TABLE 8-continued
Further compounds of Formula I (X is CH₂ and Y is C=O) prepared in excellent yields by following the same procedure as in example 10.
| Example No | Structure | ELSD Retention time/ min |
|---|---|---|
| 118 | 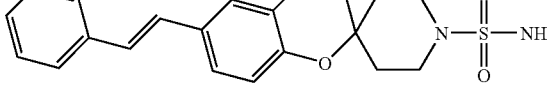 | 5.76 |
| 119 | 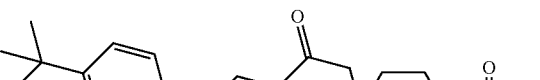 | 6.43 |
| 120 | 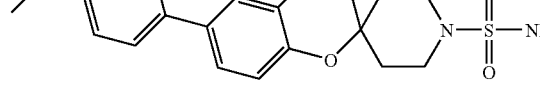 | 4.91 |
| 121 | 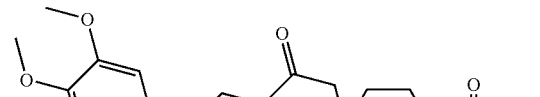 | 6.20 |
| 122 | 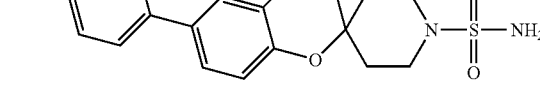 | 6.14 |
| 123 | 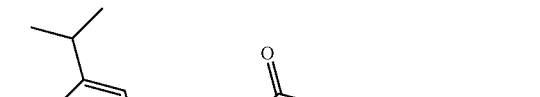 | 4.93 |
| 124 | 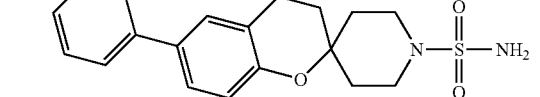 | 6.02 |
| 125 | 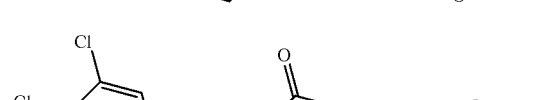 | 4.96 |

TABLE 8-continued

Further compounds of Formula I (X is CH₂ and Y is C=O) prepared in excellent yields by following the same procedure as in example 10.

| Example No | Structure | ELSD Retention time/min |
|---|---|---|
| 126 | 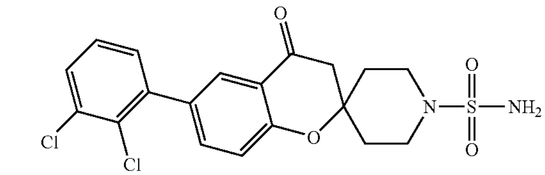 | 5.92 |
| 127 | 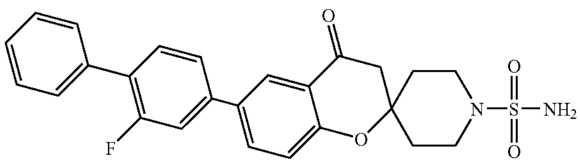 | 6.27 |
| 128 | 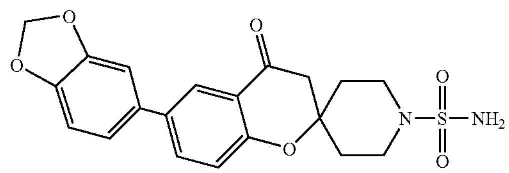 | 5.23 |

EXAMPLE I

| Capsules containing Compound 1 | |
|---|---|
| Compound 1 | 70 mg |
| Corn starch | 60 mg |
| Lactose | 250 mg |
| Ethylacetate (=EA) | q.s. |

The active substance, the corn starch and the lactose are processed into a homogeneous pasty mixture using EA. The paste is ground and the resulting granules are placed on a suitable tray and dried at 45° C. in order to remove the solvent. The dried granules are passed through a crusher and mixed in a mixer with the further following auxiliaries:

| Talcum | 5 mg |
|---|---|
| Magnesium stearate | 5 mg |
| Corn starch | 10 mg | and are then poured into 400 mg capsules (=capsule size 0).

EXAMPLE II

| Capsules containing Compound 86 | |
|---|---|
| Compound 86 | 70 mg |
| Corn starch | 60 mg |
| Lactose | 250 mg |
| Ethylacetate (=EA) | q.s. |

The active substance, the corn starch and the lactose are processed into a homogeneous pasty mixture using EA. The paste is ground and the resulting granules are placed on a suitable tray and dried at 45° C. in order to remove the solvent. The dried granules are passed through a crusher and mixed in a mixer with the further following auxiliaries:

| Talcum | 5 mg |
|---|---|
| Magnesium stearate | 5 mg |
| Corn starch | 10 mg | and are then poured into 400 mg capsules (=capsule size 0).

The foregoing description and examples have been set forth merely to illustrate the invention and are not intended to be limiting. Since modifications of the disclosed embodiments incorporating the spirit and substance of the invention may occur to persons skilled in the art, the invention should be construed broadly to include all variations within the scope of the appended claims and equivalents thereof.

What is claimed is:

1. A compound corresponding to Formula I:

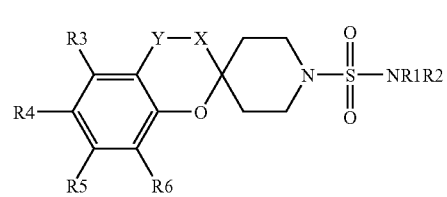

I wherein

R1 and R2 are independently selected from the group consisting of hydrogen, $C_1$ to $C_4$ alkyl, and $C_4$ to $C_7$ cycloalkyl, or R1 and R2 together form a 5 or 6-membered ring which optionally may contain 1 or 2 heteroatoms independently selected from the group consisting of nitrogen and oxygen, and which optionally also may be substituted by aryl optionally substituted with one to three substituents independently selected from the group consisting of hydrogen, amino, halogen, $C_1$ to $C_4$ alkyl, $C_1$ to $C_4$ alkoxy, oxyaryl, $C_1$ to $C_4$ mercapto, C(O)H, trifluoromethyl, —N—C(O)$C_{1-4}$alkyl, $C_2$ to $C_4$ alkenyl, C(O)$C_{1-4}$alkyl, aryl, cyano, nitro, and $C_1$ to $C_4$ alkylsulfonyl; heteroaryl optionally substituted with halogen, trifluoromethyl, cyano, $C_1$ to $C_4$ alkyl or $C_1$ to $C_4$ alkoxy; or arylenehalogenalkyl;

R3 to R6 are independently selected from the group consisting of hydrogen; halogen; $C_1$ to $C_4$ alkyl; $C_2$ to $C_4$ alkenyl optionally substituted with aryl; $C_1$ to $C_4$ alkoxy; $C_1$ to $C_4$ alkoxy substituted with halogen, provided that the alpha-carbon atom is not substituted by any halogen other than fluorine; $C_2$ to $C_4$ alkinyl; $C_1$ to $C_4$ NSO$_2$alkyl; NH$_2$; NO$_2$; $C_1$ to $C_4$ aminoalkyl; $C_2$ to $C_8$ aminodialkyl; cyano; oxyaryl; oxyalkylenearyl; oxyarylenealkyl; oxyalkylenearyleneoxy; $C_2$ to $C_8$ ester; $C_1$ to $C_8$ amido; $C_2$ to $C_8$ oxyalkylenecarbonylalkyl; $C_2$ to $C_8$ oxyalkyleneoxyalkyl; $C_1$ to $C_4$ amidooxyalkyl; aryl optionally substituted with one to three substituents independently selected from the group consisting of hydrogen, amino, halogen, $C_1$ to $C_4$ alkyl, $C_1$ to $C_4$ alkoxy, oxyaryl, $C_1$ to $C_4$ mercapto, C(O)H, trifluoromethyl, —N—C(O)$C_{1-4}$alkyl, $C_2$ to $C_4$ alkenyl, C(O)$C_{1-4}$alkyl, aryl, cyano, nitro, and $C_1$ to $C_4$ alkylsulfonyl; heteroaryl optionally substituted with halogen, trifluoromethyl, cyano, $C_1$ to $C_4$ alkyl or $C_1$ to $C_4$ alkoxy; condensed aryl optionally substituted with halogen, trifluoromethyl, cyano, $C_1$ to $C_4$ alkyl or $C_1$ to $C_4$ alkoxy; and condensed heteroaryl optionally substituted with halogen, trifluoromethyl, cyano, $C_1$ to $C_4$ alkyl or $C_1$ to $C_4$ alkoxy; or R3 and R6 have the same meanings as above, and R4 and R5 together form a 5 or 6-membered ring which optionally may contain from 1 to 3 heteroatoms independently selected from the group consisting of nitrogen, oxygen and sulfur, and which optionally may include 1 or 2 double bonds, and which also may contain a carbonyl group, and which also may be substituted by $C_1$ to $C_4$ alkyl, $C_1$ to $C_4$ halogenalkyl, aryl optionally substituted with one to three substituents independently selected from the group consisting of hydrogen, amino, halogen, $C_1$ to $C_4$ alkyl, $C_1$ to $C_4$ alkoxy, oxyaryl, $C_1$ to $C_4$ mercapto, C(O)H, trifluoromethyl, —N—C(O)$C_{1-4}$alkyl, $C_2$ to $C_4$ alkenyl, C(O)$C_{1-4}$alkyl, aryl, cyano, nitro, and $C_1$ to $C_4$ alkylsulfonyl; and/or heteroaryl optionally substituted with halogen, trifluoromethyl, cyano, $C_1$ to $C_4$ alkyl or $C_1$ to $C_4$ alkoxy; or R5 and R6 have the same meanings as above, and R3 and R4 together form a 5 or 6-membered ring which optionally may contain from 1 to 3 heteroatoms independently selected from the group consisting of nitrogen, oxygen and sulfur, and which optionally may include 1 or 2 double bonds, and which also may contain a carbonyl group, and which also may be substituted by $C_1$ to $C_4$ alkyl, $C_1$ to $C_4$ halogenalkyl, aryl optionally substituted with one to three substituents independently selected from the group consisting of hydrogen, amino, halogen, $C_1$ to $C_4$ alkyl, $C_1$ to $C_4$ alkoxy, oxyaryl, $C_1$ to $C_4$ mercapto, C(O)H, trifluoromethyl, —N—C(O)$C_{1-4}$alkyl, $C_2$ to $C_4$ alkenyl, C(O)$C_{1-4}$alkyl, aryl, cyano, nitro, and $C_1$ to $C_4$ alkylsulfonyl; and/or heteroaryl optionally substituted with halogen, trifluoromethyl, cyano, $C_1$ to $C_4$ alkyl or $C_1$ to $C_4$ alkoxy; or R3 and R4 have the same meanings as above, and R5 and R6 together form a 5 or 6-membered ring which optionally may contain from 1 to 3 heteroatoms independently selected from the group consisting of nitrogen, oxygen and sulfur, and which optionally may include 1 or 2 double bonds, and which also may contain a carbonyl group, and which also may be substituted by $C_1$ to $C_4$ alkyl, $C_1$ to $C_4$ halogenalkyl, aryl optionally substituted with one to three substituents independently selected from the group consisting of hydrogen, amino, halogen, $C_1$ to $C_4$ alkyl, $C_1$ to $C_4$ alkoxy, oxyaryl, $C_1$ to $C_4$ mercapto, C(O)H, trifluoromethyl, —N—C(O)$C_{1-4}$alkyl, $C_2$ to $C_4$ alkenyl, C(O)$C_{1-4}$alkyl, aryl, cyano, nitro, and $C_1$ to $C_4$ alkylsulfonyl; and/or heteroaryl optionally substituted with halogen, trifluoromethyl, cyano, $C_1$ to $C_4$ alkyl or $C_1$ to $C_4$ alkoxy; and Y—X is selected from the group consisting of HC=CH, CH$_2$—CH$_2$, O=C—CH$_2$, and (HO)(H)C—CH$_2$;

or a physiologically acceptable salt thereof.

2. A compound according to claim 1, wherein

R1 and R2 are independently selected from the group consisting of hydrogen, $C_1$ to $C_4$ alkyl, $C_4$ to $C_7$ cycloalkyl, or R1 and R2 together form a 5 or 6-membered ring which optionally may contain 1 or 2 heteroatoms independently selected from the group consisting of nitrogen and oxygen, and which also may be substituted by aryl optionally substituted with one to three substituents independently selected from the group consisting of hydrogen, amino, halogen, $C_1$ to $C_4$ alkyl, $C_1$ to $C_4$ alkoxy, oxyaryl, $C_1$ to $C_4$ mercapto, C(O)H, trifluoromethyl, —N—C(O)$C_{1-4}$alkyl, $C_2$ to $C_4$ alkenyl, C(O)$C_{1-4}$ alkyl, aryl, cyano, nitro, and $C_1$ to $C_4$ alkylsulfonyl; heteroaryl optionally substituted with halogen, trifluoromethyl, cyano, $C_1$ to $C_4$ alkyl or $C_1$ to $C_4$ alkoxy; or arylenehalogenalkyl;

R3 to R6 are independently selected from the group consisting of hydrogen, fluorine, chlorine, bromine, methyl, ethyl, propyl, butyl, ethylene, propylene, methoxy, ethoxy, propoxy, ethinyl, propinyl, butinyl, NSO$_2$CH$_3$, NH$_2$, NO$_2$, aminomethyl, aminoethyl, aminopropyl, aminobutyl, aminodimethyl, aminodiethyl, aminodipropyl, aminodibutyl, cyano, oxyphenyl, oxybenzyl, oxyethylenephenyl, oxyphenylenemethyl, oxyphenylenemethoxy, acetyl, amidomethyl, amidoethyl, oxymethylenecarbonylmethyl, oxyethylenecarbonylmethyl, oxymethylenecarbonylethyl, oxyethylenecarbonylethyl, oxymethylene-oxymethyl, oxymethyleneoxyethyl, oxyethyleneoxymethyl, oxyethyleneoxyethyl, amidooxymethyl, and amidooxyethyl; and Y—X is selected from the group consisting of: HC=CH, CH$_2$—CH$_2$, O=C—CH$_2$, and (HO)(H)C—CH$_2$.

3. A compound according to claim 1, wherein:

R1 and R2 are both H;

R3 to R6 are independently selected from the group consisting of: hydrogen, halogen and $C_1$ to $C_4$ alkoxy; and Y—X is O=C—CH$_2$.

4. A compound according to claim 1, wherein:

R4 is selected from the group consisting of hydrogen, chlorine, bromine, and methoxy; and R5 is selected from the group consisting of hydrogen and bromine.

5. A compound according to claim 1, wherein:
R1 and R2 are independently selected from the group consisting of hydrogen, $C_1$ to $C_4$ alkyl, $C_4$ to $C_7$ cycloalkyl, or
R1 and R2 together form a 5 or 6-membered ring which optionally may contain 1 or 2 heteroatoms independently selected from the group consisting of nitrogen and oxygen, and which also may be substituted by aryl optionally substituted with one to three substituents independently selected from the group consisting of hydrogen, amino, halogen, $C_1$ to $C_4$ alkyl, $C_1$ to $C_4$ alkoxy, oxyaryl, $C_1$ to $C_4$ mercapto, C(O)H, trifluoromethyl, —N—C(O)$C_{1-4}$alkyl, $C_2$ to $C_4$ alkenyl, C(O)$C_{1-4}$ alkyl, aryl, cyano, nitro, and $C_1$ to $C_4$ alkylsulfonyl; heteroaryl optionally substituted with halogen, trifluoromethyl, cyano, $C_1$ to $C_4$ alkyl or $C_1$ to $C_4$ alkoxy; or arylenehalogenalkyl;
R3, R5 and R6 are independently selected from the group consisting of hydrogen; halogen; $C_1$ to $C_4$ alkyl; $C_2$ to $C_4$ alkenyl; $C_1$ to $C_4$ alkoxy; $C_1$ to $C_4$ alkoxy substituted with halogen, provided that the alpha-carbon atom is not substituted by any halogen other than fluorine; $C_2$ to $C_4$ alkinyl; $C_1$ to $C_4$ NSO$_2$alkyl; NH$_2$; NO$_2$; $C_1$ to $C_4$ aminoalkyl; $C_2$ to $C_8$ aminodialkyl; cyano; oxyaryl; oxyalkylenearyl; oxyarylenealkyl; oxyalkylenearylenealkoxy; $C_2$ to $C_8$ ester; $C_1$ to $C_8$ amido; $C_2$ to $C_8$ oxyalkylenecarbonylalkyl; $C_2$ to $C_8$ oxyalkyleneoxyalkyl; and $C_1$ to $C_4$ amidooxyalkyl;
R4 is selected from the group consisting of:
  (a) phenyl optionally substituted with one to three substituents independently selected from the group consisting of hydrogen, amino, halogen, $C_1$ to $C_4$ alkyl, $C_1$ to $C_4$ alkoxy, oxyaryl, $C_1$ to $C_4$ mercapto, C(O)H, trifluoromethyl, —N—C(O)$C_{1-4}$alkyl, $C_2$ to $C_4$ alkenyl, C(O)$C_{1-4}$alkyl, and aryl; and
  (b) 1-naphthyl, 2-naphthyl, 2-pyridyl, 3-pyridyl, 4-pyridyl, 2-thiophenyl, 3-thiophenyl, quinoline, isoquinoline, benzo[b]thiophene, 1,3-dihydro-benzo[c]thiophene, 1-dibenzofuran, 2-dibenzofuran, 3-dibenzofuran, and 4-dibenzofuran, each optionally substituted with one to three substituents selected from the group consisting of hydrogen, amino, halogen, $C_1$ to $C_4$ alkyl, $C_1$ to $C_4$ alkoxy, oxyaryl, $C_1$ to $C_4$ mercapto, C(O)H, trifluoromethyl, —N—C(O)$C_{1-4}$ alkyl, $C_2$ to $C_4$ alkenyl, C(O)$C_{1-4}$alkyl, and aryl; and
Y—X is selected from the group consisting of HC=CH, CH$_2$—CH$_2$, O=C—CH$_2$, and (HO)(H)C—CH$_2$.

6. A compound according to claim 5 wherein:
R1, R2, R3, R5 and R6 are each hydrogen; and
R4 is selected from the group consisting of:
  (a) phenyl optionally substituted with one to three substituents independently selected from the group consisting of hydrogen, amino, halogen, $C_1$ to $C_4$ alkyl, $C_1$ to $C_4$ alkoxy, oxyaryl, C1 to C4 mercapto, C(O)H, trifluoromethyl, —N—C(O)$C_{1-4}$alkyl, C2 to C4 alkenyl, C(O)$C_{1-4}$alkyl, aryl; and
  (b) 1-naphthyl, 2-naphthyl, 2-pyridyl, 3-pyridyl, 4-pyridyl, 2-thiophenyl, 3-thiophenyl, quinoline, isoquinoline, benzo[b]thiophene, 1,3-dihydro-benzo[c]thiophene, 1-dibenzofuran, 2-dibenzofuran, 3-dibenzofuran, 4-dibenzofuran; and
Y—X is O=C—CH$_2$.

7. A pharmaceutical composition comprising a compound according to claim 1 and at least one pharmaceutically acceptable carrier or auxiliary.

8. A pharmaceutical composition comprising a compound according to claim 2 and at least one pharmaceutically acceptable carrier or auxiliary.

9. A pharmaceutical composition comprising a compound according to claim 3 and at least one pharmaceutically acceptable carrier or auxiliary.

10. A pharmaceutical composition comprising a compound according to claim 4 and at least one pharmaceutically acceptable carrier or auxiliary.

11. A pharmaceutical composition comprising a compound according to claim 5 and at least one pharmaceutically acceptable carrier or auxiliary.

12. A pharmaceutical composition comprising a compound according to claim 6 and at least one pharmaceutically acceptable carrier or auxiliary.

13. A process for preparing a compound according to claim 1, said process comprising:
reacting a benzopyran compound of Formula II,

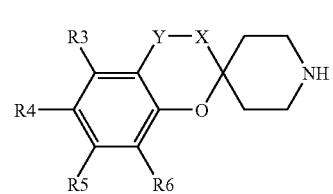

wherein R3 to R6, X and Y have the meanings given in claim 1,
(a) with a sulfamide to yield a compound of Formula I, or
(b) with a compound of formula III

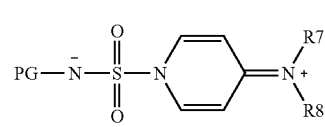

wherein
R7 and R8 are independently $C_1$ to $C_6$ alkyl or $C_3$ to $C_8$ cycloalkyl, and
PG denotes a protecting group,
to obtain an intermediate compound, and
subsequently cleaving off the PG-group from the intermediate compound to yield a compound of formula I, or
(c) with a sulfamoylchloride of Formula IV

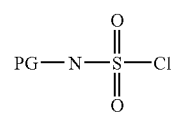

wherein PG denotes a protecting group,
to obtain an intermediate product, and
subsequently cleaving off the protecting group from the intermediate product to yield a compound of formula I, or (d) with a sulfamoylchloride of Formula IVa

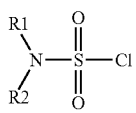

IVa wherein R1 and R2 have the above meanings,
to yield a compound of formula I, or
(e) reacting a compound of Formula I wherein at least one of R3 to R6 is a bromo, chloro or iodo atom, with a compound of formula IX

W—B(OH)$_2$    IX wherein W is selected from the group consisting of aryl optionally substituted with one to three substituents independently selected from the group consisting of hydrogen, amino, halogen, $C_1$ to $C_4$ alkyl, $C_1$ to $C_4$ alkoxy, oxyaryl, $C_1$ to $C_4$ mercapto, C(O)H, trifluoromethyl, —N—C(O)$C_{1-4}$alkyl, $C_2$ to $C_4$ alkenyl, C(O)$C_{1-4}$alkyl, aryl, cyano, nitro, and $C_1$ to $C_4$ alkylsulfonyl; heteroaryl optionally substituted with halogen, trifluoromethyl, cyano, $C_1$ to $C_4$ alkyl or $C_1$ to $C_4$ alkoxy; condensed aryl; and condensed heteroaryl;
to yield a compound of formula I, wherein said bromo, chloro or iodo atom of the starting compound of Formula I is replaced by W;
and if the product is a free base of Formula I, optionally converting the free base into a physiologically acceptable salts, or if the product is a salt, optionally converting the salt into a free base of Formula I.

14. A process according to claim 13, wherein
R1 and R2 are independently selected from the group consisting of hydrogen, $C_1$ to $C_4$ alkyl, $C_4$ to $C_7$ cycloalkyl, or
R1 and R2 together form a 5 or 6-membered ring which optionally may contain 1 or 2 heteroatoms independently selected from the group consisting of nitrogen and oxygen, and which also may be substituted by aryl optionally substituted with one to three substituents independently selected from the group consisting of hydrogen, amino, halogen, $C_1$ to $C_4$ alkyl, $C_1$ to $C_4$ alkoxy, oxyaryl, $C_1$ to $C_4$ mercapto, C(O)H, trifluoromethyl, —N—C(O)$C_{1-4}$alkyl, $C_2$ to $C_4$ alkenyl, C(O)$C_{1-4}$ alkyl, aryl, cyano, nitro, and $C_1$ to $C_4$ alkylsulfonyl; heteroaryl optionally substituted with halogen, trifluoromethyl, cyano, $C_1$ to $C_4$ alkyl or $C_1$ to $C_4$ alkoxy; or arylenehalogenalkyl;
R3 to R6 are independently selected from the group consisting of hydrogen, fluorine, chlorine, bromine, methyl, ethyl, propyl, butyl, ethylene, propylene, methoxy, ethoxy, propoxy, ethinyl, propinyl, butinyl, NSO$_2$CH$_3$, NH$_2$, NO$_2$, aminomethyl, aminoethyl, aminopropyl, aminobutyl, aminodimethyl, aminodiethyl, aminodipropyl, aminodibutyl, cyano, oxyphenyl, oxybenzyl, oxyethylenephenyl, oxyphenylenemethyl, oxyphenylenemethoxy, acetyl, amidomethyl, amidoethyl, oxymethylenecarbonylmethyl, oxyethylenecarbonylmethyl, oxyethylene-carbonylethyl, oxyethylenecarbonylethyl, oxymethyleneoxymethyl, oxymethyleneoxyethyl, oxyethyleneoxymethyl, oxyethyleneoxyethyl, amidooxymethyl, and amidooxyethyl; and
Y—X is selected from the group consisting of: HC=CH, CH$_2$—CH$_2$, O=C—CH$_2$, and (HO)(H)C—CH$_2$.

15. A process according to claim 13, wherein:
R1 and R2 are both H;
R3 to R6 are independently selected from the group consisting of: hydrogen, halogen and $C_1$ to $C_4$ alkoxy; and
Y—X is O=C—CH$_2$.

16. A process according to claim 13, wherein:
R4 is selected from the group consisting of hydrogen, chlorine, bromine, and methoxy; and
R5 is selected from the group consisting of hydrogen and bromine.

17. A process according to claim 13, wherein:
R1 and R2 are independently selected from the group consisting of hydrogen, $C_1$ to $C_4$ alkyl, $C_4$ to C7 cycloalkyl, or
R1 and R2 together form a 5 or 6-membered ring which optionally may contain 1 or 2 heteroatoms independently selected from the group consisting of nitrogen and oxygen, and which also may be substituted by aryl optionally substituted with one to three substituents independently selected from the group consisting of hydrogen, amino, halogen, $C_1$ to $C_4$ alkyl, $C_1$ to $C_4$ alkoxy, oxyaryl, $C_1$ to $C_4$ mercapto, C(O)H, trifluoromethyl, —N—C(O)$C_{1-4}$alkyl, $C_2$ to $C_4$ alkenyl, C(O)$C_{1-4}$ alkyl, aryl, cyano, nitro, and $C_1$ to $C_4$ alkylsulfonyl; heteroaryl optionally substituted with halogen, trifluoromethyl, cyano, $C_1$ to $C_4$ alkyl or $C_1$ to $C_4$ alkoxy; or arylenehalogenalkyl;
R3, R5 and R6 are independently selected from the group consisting of hydrogen; halogen; $C_1$ to $C_4$ alkyl; $C_2$ to $C_4$ alkenyl; $C_1$ to $C_4$ alkoxy; $C_1$ to $C_4$ alkoxy substituted with halogen, provided that the alpha-carbon atom is not substituted by any halogen other than fluorine; $C_2$ to $C_4$ alkinyl; $C_1$ to $C_4$ NSO$_2$alkyl; NH$_2$; NO$_2$; $C_1$ to $C_4$ aminoalkyl; $C_2$ to $C_8$ aminodialkyl; cyano; oxyaryl; oxyalkylenearyl; oxyarylenealkyl; oxyalkylenearylenealkoxy; $C_2$ to $C_8$ ester; $C_1$ to $C_8$ amido; $C_2$ to $C_8$ oxyalkylenecarbonylalkyl; $C_2$ to $C_8$ oxyalkyleneoxyalkyl; and $C_1$ to $C_4$ amidooxyalkyl;
R4 is selected from the group consisting of:
(a) phenyl optionally substituted with one to three substituents independently selected from the group consisting of hydrogen, amino, halogen, $C_1$ to $C_4$ alkyl, $C_1$ to $C_4$ alkoxy, oxyaryl, $C_1$ to $C_4$ mercapto, C(O)H, trifluoromethyl, —N—C(O)$C_{1-4}$alkyl, $C_2$ to $C_4$ alkenyl, C(O)$C_{1-4}$alkyl, and aryl; and
(b) 1-naphthyl, 2-naphthyl, 2-pyridyl, 3-pyridyl, 4-pyridyl, 2-thiophenyl, 3-thiophenyl, quinoline, isoquinoline, benzo[b]thiophene, 1,3-dihydro-benzo[c]thiophene, 1-dibenzofuran, 2-dibenzofuran, 3-dibenzofuran, and 4-dibenzofuran, each optionally substituted with one to three substituents selected from the group consisting of hydrogen, amino, halogen, $C_1$ to $C_4$ alkyl, $C_1$ to $C_4$ alkoxy, oxyaryl, $C_1$ to $C_4$ mercapto, C(O)H, trifluoromethyl, —N—C(O)$C_{1-4}$ alkyl, $C_2$ to $C_4$ alkenyl, C(O)$C_{1-4}$alkyl, and aryl; and
Y—X is selected from the group consisting of HC=CH, CH$_2$—CH$_2$, O=C—CH$_2$, and (HO)(H)C—CH$_2$.

18. A process according to claim 17 wherein:
R1, R2, R3, R5 and R6 are each hydrogen; and
R4 is selected from the group consisting of:
(a) phenyl optionally substituted with one to three substituents independently selected from the group consisting of hydrogen, amino, halogen, $C_1$ to $C_4$ alkyl, $C_1$ to $C_4$ alkoxy, oxyaryl, C1 to C4 mercapto, C(O)H, trifluoromethyl, —N—C(O)$C_{1-4}$alkyl, C2 to C4 alkenyl, C(O)$C_{1-4}$alkyl, aryl; and (b) 1-naphthyl, 2-naphthyl, 2-pyridyl, 3-pyridyl, 4-pyridyl, 2-thiophenyl, 3-thiophenyl, quinoline, isoquinoline, benzo[b]thiophene, 1,3-dihydro-benzo[c]thiophene, 1-dibenzofuran, 2-dibenzofuran, 3-dibenzofuran, 4-dibenzofuran; and Y—X is O=C—CH$_2$.

19. A method of treating a condition or disease state selected from the group consisting of glaucoma, epilepsy, neuropathic pain, obesity, type II diabetes and metabolic syndrome, in a mammal in need thereof, said method comprising administering to said mammal a pharmaceutically effective amount of a compound according to claim 1.

20. A method according to claim 19, wherein said mammal is a human.

* * * * *